(12) United States Patent
Bai et al.

(10) Patent No.: US 11,613,719 B2
(45) Date of Patent: *Mar. 28, 2023

(54) SELF-LUBRICATING MEDICAL ARTICLES

(71) Applicant: Becton, Dickinson and Company, Franklin Lakes, NJ (US)

(72) Inventors: He Bai, Sandy, UT (US); Marc Weimer, South Jordan, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 703 days.

This patent is subject to a terminal disclaimer.

(21) Appl. No.: 16/577,824

(22) Filed: Sep. 20, 2019

(65) Prior Publication Data

US 2020/0095515 A1 Mar. 26, 2020

Related U.S. Application Data

(60) Provisional application No. 62/735,332, filed on Sep. 24, 2018.

(51) Int. Cl.
*C10M 105/76* (2006.01)
*A61L 29/14* (2006.01)
(Continued)

(52) U.S. Cl.
CPC ........... *C10M 105/76* (2013.01); *A61L 29/06* (2013.01); *A61L 29/085* (2013.01); *A61L 29/14* (2013.01);
(Continued)

(58) Field of Classification Search
CPC ........... C08G 18/7621; C08G 18/42; C08G 18/6674; C08G 18/289; C08G 18/7671;
(Continued)

(56) References Cited

U.S. PATENT DOCUMENTS 3,071,856 A 1/1963 Fischbein
3,361,700 A 1/1968 Archer et al.
(Continued)

FOREIGN PATENT DOCUMENTS

AU 2010224421 B9 12/2010
AU 2015206417 B2 7/2015
(Continued)

OTHER PUBLICATIONS

Kucinska-Lipka et al. ("Thermal and mechanical properties of polyurethanes modified with L-Ascorbic acid" in J. Therm Anal Calorim (2017), 127:1631-1638). (Year: 2017).*
(Continued)

*Primary Examiner* — Blessing M Fubara
(74) *Attorney, Agent, or Firm* — Servilla Whitney LLC

(57) ABSTRACT

Medical articles formed from a polyurethane-based resin including a modifying oligomer provide enhanced properties. A modifying oligomer incorporated into a backbone, as a side chain, or both of the polyurethane-based resin formed by a diisocyanate, a polyglycol, and a diol chain extender has at least one, preferably two, alcohol moieties (C—OH) and a functional moiety. Exemplary modifying oligomers are: a diol-containing perfluoropolyether incorporated into the backbone, a monofunctional polysiloxane (e.g., mono-dialcohol-terminated polydimethylsiloxane) incorporated as the side chain, and combinations thereof. Medical articles herein are self-lubricating and/or anti-fouling.

15 Claims, 6 Drawing Sheets

(51) Int. Cl.
*A61L 29/08* (2006.01)
*C10M 171/00* (2006.01)
*C08G 18/48* (2006.01)
*A61L 31/06* (2006.01)
*C08G 18/76* (2006.01)
*C08G 18/75* (2006.01)
*C08G 18/28* (2006.01)
*A61L 29/06* (2006.01)
*C10N 40/00* (2006.01)

(52) U.S. Cl.
CPC ............ *A61L 31/06* (2013.01); *C08G 18/289* (2013.01); *C08G 18/4854* (2013.01); *C08G 18/755* (2013.01); *C08G 18/7621* (2013.01); *C10M 171/00* (2013.01); *A61L 2400/10* (2013.01); *C10M 2213/06* (2013.01); *C10N 2040/50* (2020.05)

(58) Field of Classification Search
CPC ................ C08G 18/755; C08G 18/758; C08G 18/3206; C08G 18/4808; C08G 18/5015; C08G 18/44; C08G 18/4854; A61L 29/06; A61L 29/14; A61L 29/085; A61L 31/06
See application file for complete search history.

(56) References Cited

U.S. PATENT DOCUMENTS

| | | |
|---|---|---|
| 3,441,142 A | 4/1969 | Oja |
| 3,562,352 A | 2/1971 | Nyilas |
| 3,574,673 A | 4/1971 | Schweiger |
| 3,616,935 A | 11/1971 | Love et al. |
| 3,617,344 A | 11/1971 | Leininger et al. |
| 3,634,123 A | 1/1972 | Eriksson et al. |
| 3,645,955 A | 2/1972 | Flynn |
| 3,755,218 A | 8/1973 | Yen et al. |
| 3,759,788 A | 9/1973 | Gajewski et al. |
| 3,810,781 A | 5/1974 | Eriksson et al. |
| 3,846,353 A | 11/1974 | Grotta |
| 4,057,595 A | 11/1977 | Rauner et al. |
| 4,100,309 A | 7/1978 | Micklus et al. |
| 4,182,787 A | 1/1980 | Goossens et al. |
| 4,188,426 A | 2/1980 | Auerbach |
| 4,250,072 A | 2/1981 | Flynn |
| 4,283,447 A | 8/1981 | Flynn |
| 4,326,532 A | 4/1982 | Hammar |
| 4,349,467 A | 9/1982 | Williams et al. |
| 4,373,009 A | 2/1983 | Winn |
| 4,454,309 A | 6/1984 | Gould et al. |
| 4,521,564 A | 6/1985 | Solomon et al. |
| 4,579,879 A | 4/1986 | Flynn |
| 4,581,390 A | 4/1986 | Flynn |
| 4,589,873 A | 5/1986 | Schwartz et al. |
| 4,613,517 A | 9/1986 | Williams et al. |
| 4,642,242 A | 2/1987 | Solomon et al. |
| 4,642,267 A | 2/1987 | Creasy et al. |
| 4,647,643 A | 3/1987 | Zdrahala et al. |
| 4,657,024 A | 4/1987 | Coneys |
| 4,664,657 A | 5/1987 | Williamitis et al. |
| 4,668,221 A | 5/1987 | Luther |
| 4,678,660 A | 7/1987 | McGary et al. |
| 4,713,402 A | 12/1987 | Solomon |
| 4,720,521 A | 1/1988 | Spielvogel et al. |
| 4,722,344 A | 2/1988 | Cambron et al. |
| 4,767,414 A | 8/1988 | Williams et al. |
| 4,841,007 A | 6/1989 | Zdrahala et al. |
| 4,842,889 A | 6/1989 | Hu et al. |
| 4,844,986 A | 7/1989 | Karakelle et al. |
| 4,865,870 A | 9/1989 | Hu et al. |
| 4,883,699 A | 11/1989 | Aniuk et al. |
| 4,925,668 A | 5/1990 | Khan et al. |
| 4,935,480 A | 6/1990 | Zdrahala et al. |
| 4,939,007 A | 7/1990 | Hu et al. |
| 4,990,537 A | 2/1991 | Okuyama et al. |
| 4,994,047 A | 2/1991 | Walker et al. |
| 5,004,456 A | 4/1991 | Botterbusch et al. |
| 5,013,306 A | 5/1991 | Solomon et al. |
| 5,026,814 A | 6/1991 | Re et al. |
| 5,032,666 A | 7/1991 | Hu et al. |
| 5,043,410 A | 8/1991 | Re et al. |
| 5,059,269 A | 10/1991 | Hu et al. |
| 5,061,254 A | 10/1991 | Karakelle et al. |
| 5,084,315 A | 1/1992 | Karimi et al. |
| 5,102,401 A | 4/1992 | Lambert et al. |
| 5,159,050 A | 10/1992 | Onwumere |
| 5,159,051 A | 10/1992 | Onwumere et al. |
| 5,226,899 A | 7/1993 | Lee et al. |
| 5,250,649 A | 10/1993 | Onwumere et al. |
| 5,262,057 A | 11/1993 | Tonelli et al. |
| 5,266,669 A | 11/1993 | Onwunaka et al. |
| 5,281,677 A | 1/1994 | Onwunaka et al. |
| 5,302,385 A | 4/1994 | Khan et al. |
| 5,322,659 A | 6/1994 | Walder et al. |
| 5,332,798 A | 7/1994 | Ferreri et al. |
| 5,453,099 A | 9/1995 | Lee et al. |
| 5,508,380 A | 4/1996 | Turri et al. |
| 5,545,708 A * | 8/1996 | Onwunaka ......... C08G 18/6674 264/165 |
| 6,207,777 B1 | 3/2001 | Shimada et al. |
| 6,261,271 B1 | 7/2001 | Solomon et al. |
| 6,268,440 B1 | 7/2001 | Kudo et al. |
| 6,287,707 B1 | 9/2001 | Luthra et al. |
| 6,579,835 B2 | 6/2003 | Scicchitano et al. |
| 7,358,306 B2 | 4/2008 | Turri et al. |
| 8,357,767 B2 | 1/2013 | Moore et al. |
| 8,691,887 B2 | 4/2014 | Ou-Yang |
| 8,754,020 B2 | 6/2014 | Ou-Yang |
| 8,821,455 B2 | 9/2014 | Burkholz et al. |
| 9,334,213 B2 | 5/2016 | Guarda et al. |
| 9,345,806 B2 | 5/2016 | Tonelli et al. |
| 2003/0018156 A1 | 1/2003 | Meijs et al. |
| 2006/0287458 A1 | 12/2006 | Moszner et al. |
| 2012/0208916 A1 | 8/2012 | Cavitt et al. |
| 2013/0158518 A1 | 6/2013 | Li et al. |
| 2013/0178125 A1 | 7/2013 | Jiang et al. |
| 2016/0024419 A1 * | 1/2016 | Hermel-Davidock ...................... C08G 18/61 508/204 |
| 2017/0107320 A1 | 4/2017 | Zhou et al. |
| 2017/0226272 A1 | 8/2017 | Cozzens et al. |
| 2018/0105665 A1 | 4/2018 | Day et al. |
| 2018/0237721 A1 | 8/2018 | Hermel-Davidock et al. |
| 2018/0296731 A1 | 10/2018 | Lim et al. |
| 2019/0111186 A1 | 4/2019 | Lyu et al. |
| 2019/0112411 A1 | 4/2019 | Chen et al. |
| 2019/0388593 A1 | 12/2019 | Miura et al. |

FOREIGN PATENT DOCUMENTS

| | | |
|---|---|---|
| CA | 2716502 C | 11/2010 |
| CA | 2937132 A1 | 7/2015 |
| CN | 102316965 A | 1/2012 |
| CN | 103242505 A | 8/2013 |
| DE | 10050495 A1 | 4/2002 |
| DE | 102016225500 A1 | 6/2018 |
| EP | 0359273 A2 | 3/1990 |
| EP | 0452123 A1 | 10/1991 |
| EP | 0548745 A2 | 6/1993 |
| GB | 2332438 A | 6/1999 |
| WO | 2012027729 A1 | 3/2012 |
| WO | 2016172460 A1 | 10/2016 |
| WO | 2017014597 A1 | 1/2017 |
| WO | 2017015072 A1 | 1/2017 |
| WO | 2017015073 A1 | 1/2017 |
| WO | 2017172740 A1 | 10/2017 |
| WO | 2018011748 A1 | 1/2018 |
| WO | 2018029133 A1 | 2/2018 |
| WO | 2018140911 A1 | 8/2018 |
| WO | 2019101771 A1 | 5/2019 |
| WO | 2020021203 A1 | 1/2020 |

(56) References Cited

FOREIGN PATENT DOCUMENTS

| WO | 2020030670 A1 | 2/2020 |
|----|---------------|--------|
| WO | 2020068617 A1 | 4/2020 |
| WO | 2020068619 A1 | 4/2020 |

OTHER PUBLICATIONS

Solvay Specialty Polymers, "FLUOROLINK® for Low Surface Energy Coatings," 2013.
Arkles, Barry, et al., "Positive Tactile Interaction Coatings", Paint & Coatings Industry magazine, Issued Jul. 2017, vol. 23, No. 7, pp. 1-8.
Tonelli, Claudio, et al., "New Perfluoropolyether Soft Segment Containing Polyurethanes", Journal of Applied Polymer Science. vol. 57, 1031-1042 (1995).
PCT International Search Report and Written Opinion in PCT/US2019/052351 dated Dec. 10, 2019, 14 pages.
PCT international Search Report and Written Opinion in PCT/US2019/052355 dated Dec. 12, 2019, 14 pages.
Vaidya, Ashish, et al., "Synthesis and Surface Properties of Environmentally Responsive Segmented Polyurethanes", Journal of Colloid and Interface Science, vol. 249, No. 1, May 1, 2002, pp. 235-245.
Non-Final Office Action in U.S. Appl. No. 16/577,826, dated Dec. 23, 2022, 10 pages.

\* cited by examiner

SELF-LUBRICATING MEDICAL ARTICLES

CROSS-REFERENCE TO RELATED APPLICATIONS

This application claims priority under 35 U.S.C. § 119(e) to U.S. Provisional Application No. 62/735,332, filed Sep. 24, 2018, the disclosure of which is incorporated herein by reference in its entirety.

TECHNICAL FIELD

The present disclosure relates to a polyurethane-based resin including a backbone of a diisocyanate, a polyglycol, and a diol chain extender, which also includes addition of at least one modifier to the backbone or as a side chain that enhances the resin characteristics. The modifier is a modifying oligomer that has at least one, preferably two, alcohol moieties (C—OH) and a functional moiety. The functional moiety may be, for example, a fluoroether or a silicone. One improved characteristic is phase separation, which concentrates a soft segment of the resin towards a surface of a medical article formed therefrom. The resulting surface of the medical article provides advantages including being self-lubricating and/or anti-fouling, which eliminates a need to separately provide functional coatings such as a lubricant and/or an anti-fouling agent.

BACKGROUND

Infusion therapy medical devices, such as syringe cannulas and catheters used for sampling or medicament administration, typically have components that are in sliding contact during use. Such devices require lubrication of the moving components and may also require lubrication of an external surface. Many medical devices are fabricated from polymeric materials that are inherently non-lubricious and require separate application of a lubricant to their surfaces for use. Examples of state-of-art surface lubrication technologies include silicone surface coating, fluorocarbon surface coating, and hydrophilic polyvinylpyrrolidone (PVP) surface coating.

Catheter-related bloodstream infections may be caused by colonization of microorganisms, which can occur in patients whose treatment includes intravascular catheters and I.V. access devices. These infections can lead to illness and excess medical costs. Impregnating catheters with various antimicrobial agents is one approach that has been implemented to prevent these infections. Another approach is surface modification technologies including direct antimicrobial agent (e.g., chlorhexidine) surface coating and coating of water insoluble quaternary ammonium salts (e.g., tridodecylmethyl ammonium chloride) as a binding agent to associate with antimicrobial agents (e.g., sodium dicloxacillin).

Some blood contact devices have the potential to generate thrombus. When blood contacts a foreign material, a complex series of events occur. These involve protein deposition, cellular adhesion and aggregation, and activation of blood coagulation schemes. Thrombogenicity has conventionally been counteracted by the use of anticoagulants such as heparin. Attachment of heparin to otherwise thrombogenic polymeric surfaces may be achieved with a coating of water insoluble quaternary ammonium salts (e.g., tridodecylmethyl ammonium chloride) onto polymer substrate surface as a binding agent to associate with heparin and synthesis of a polymer substrate containing tertiary amino functional groups to be able to bind heparin.

Surface modification technology to apply lubricious, antimicrobial, and/or non-thrombogenic coating onto a medical device surface involves several issues related to the coating technique: (i) the extra step of post-coating for surface modification complicates the medical device manufacturing process and increases cost and (ii) aqueous or organic solvents are required in the coating process. When aqueous solution can be used, it means that the coating composition is water-soluble, which will lose its integrity in human body environment. If strong polar organic solvent has to be used, the solvent can attack the polymer substrate material and deteriorate the mechanical strength of the overall medical device. In addition, organic solvent usage is disadvantageous with respect to environmental, health, and safety in medical device manufacturing process. Another issue with external coatings is migration and/or leakage of active lubricious, antimicrobial and/or non-thrombogenic agent, and the medical device could lose its advantageous properties over time.

Elimination of secondary coating steps has advantages in reducing costs of manufacture. In addition, secondary raw materials such as solvents and coating agents can be eliminated, which reduces costs, leads to environmental benefits, and improves work-place safety.

Thus, there is a need for polymeric resins, in particular polyurethane resins, that can provide self-lubricating and/or self-anti-fouling characteristics while allowing for tailorability without additives or an extra coating.

SUMMARY

Provided are medical articles, for example, catheter tubing. Non-limiting examples of catheter tubing include: peripheral intravenous (IV) catheters; intravascular catheters; central venous catheters including tri-lumen, bi-lumen, and single lumen; and urinary catheters. Vascular access devices may use catheter tubing as disclosed herein in conjunction with one or more components such as needles and/or guidewires.

Various embodiments are listed below. It will be understood that the embodiments listed below may be combined not only as listed below, but in other suitable combinations in accordance with the scope of the invention.

In an aspect, a medical article is formed from a polyurethane-based resin, which is a reaction product of the following ingredients: a diisocyanate; a diol chain extender; a polyglycol; and a modifying oligomer incorporated into a backbone, as a side chain, or both of the polyurethane-based resin formed by the diisocyanate, the polyglycol, and the diol chain extender, the modifying oligomer having an alcohol (C—OH) moiety and a functional moiety. A hard segment content is in the range of from 25% to 75% by weight and a soft segment content of the resin is in the range of from 75% to 25% by weight; and the medical article is effective as a self-lubricating and/or self-anti-fouling medical article.

A concentration of the modifying oligomer of the polyurethane-based resin at a surface of the medical article may be higher than a theoretical concentration based on uniform distribution of ingredients of the polyurethane-based resin.

In one or more embodiments, the functional moiety comprises a fluoroether, a silicone, or a combination thereof.

The modifying oligomer may be selected from the group consisting of: a diol-containing perfluoropolyether incorporated into the backbone, a monofunctional polysiloxane incorporated as the side chain, and combinations thereof.

The modifying oligomer may be present in an amount ranging from about 0.1 to about 10 weight percent of the overall composition of the polyurethane-based resin.

In an aspect, a medical article is formed from a polyurethane-based resin, which is a reaction product of the following ingredients: a diisocyanate; a diol chain extender; a polyglycol; and a modifying oligomer incorporated into a backbone, as a side chain, or both of the polyurethane-based resin formed by the diisocyanate, the polyglycol, and the diol chain extender. A hard segment content is in the range of from 25% to 75% by weight and a soft segment content of the resin is in the range of from 75% to 25% by weight; and the medical article has a contact angle with water that is 90° or greater.

In one or more embodiments, the modifying oligomer has an alcohol (C—OH) moiety and a functional moiety.

In one or more embodiments, the functional moiety comprises a fluoroether, a silicone, or a combination thereof.

The modifying oligomer may be selected from the group consisting of: a diol-containing perfluoropolyether incorporated into the backbone, a monofunctional polysiloxane incorporated as the side chain, and combinations thereof.

A concentration of the modifying oligomer of the polyurethane-based resin at a surface of the medical article may be higher than a theoretical concentration based on uniform distribution of ingredients of the polyurethane-based resin.

A medical article of any embodiment herein may comprise a coefficient of static friction that is 0.28 or less.

A medical article of any embodiment herein may comprise a water sorption of 2.2% by weight or less.

A medical article of any embodiment herein may be non-hydratable.

A medical article of any embodiment herein may be effective to reduce bacterial biofilm colony formation.

A medical article of any embodiment herein may be effective to reduce thrombosis formation.

Another aspect is a method of infusion therapy comprising: infusing a material from a medical article according to any embodiment into a patient.

The method may be conducted in the presence or absence of a separate lubricant coated on the medical article.

The method may be conducted in the presence or absence of a separate anti-fouling agent coated on the medical article.

DETAILED DESCRIPTION

Figure 1:
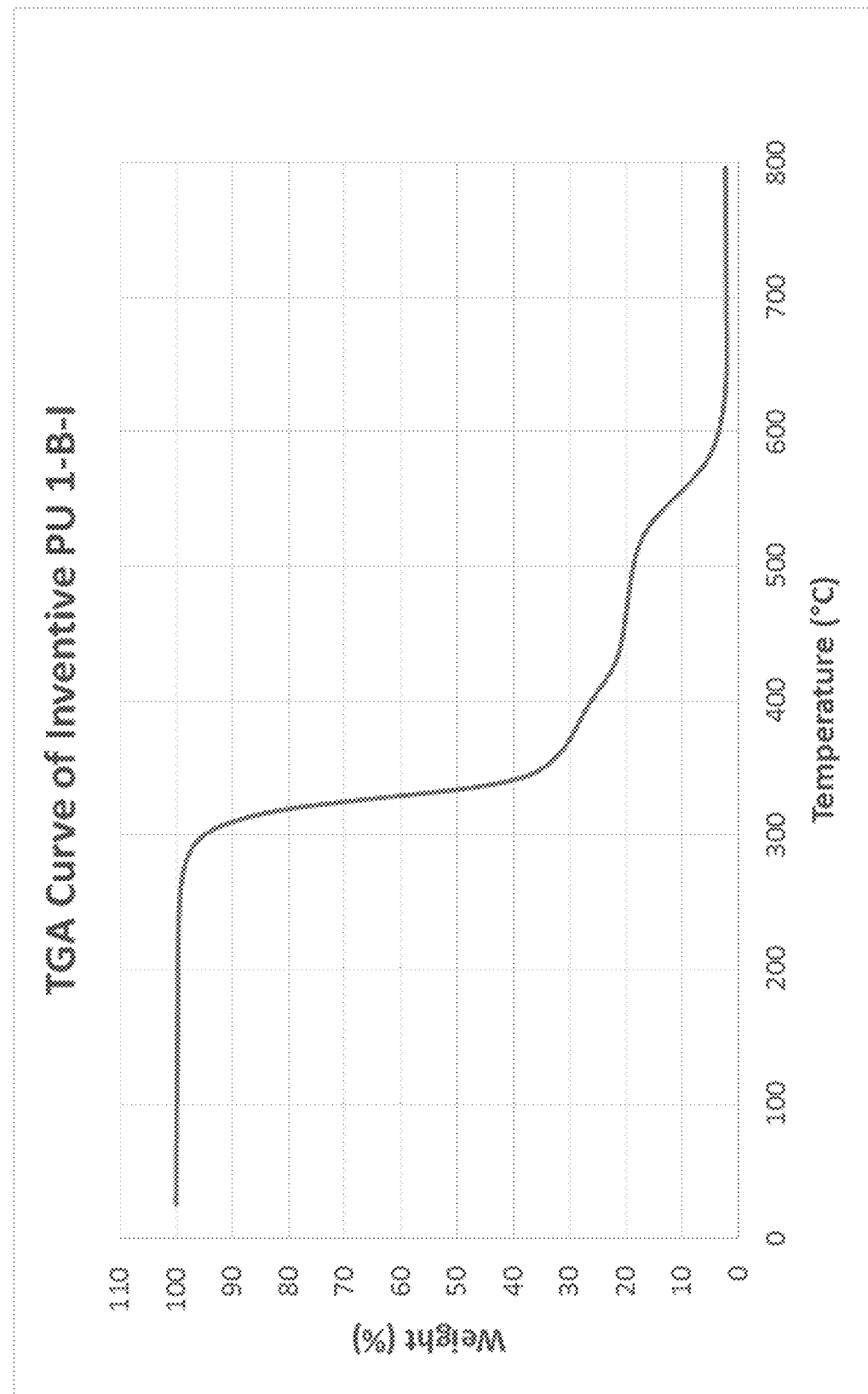
FIG. 1 is a thermogravimetric analysis (TGA) curve, weight (%) versus temperature (° C.) for an embodiment.

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

Polyglycols include but are not limited to: polyalkylene glycol, polyester glycol, and polycarbonate glycol. A non-limiting specific example of polyalkylene glycol is polyether glycol. A polyether glycol is a moderate molecular weight oligomer derived from an alkylene oxide, containing both ether linkages and glycol termination.

A chain extender is a short chain (low molecular weight) branched or unbranched diol, diamine or amino alcohol of up to 10 carbon atoms or mixtures thereof. Such hydroxyl- and/or amine-terminated compounds are used during polymerization to impart desired properties to a polymer.

A modifying oligomer (moderate molecular weight) is a compound that enhances a basic polyurethane structure of a diisocyanate; a diol chain extender; and a polyglycol. Modifying oligomers, which are different from polyglycols, contain functional moieties (e.g., fluoroether and/or silicone) that migrate onto the polyurethane surface to render the resulting medical article desirable surface properties. Modifying oligomers used herein have at least one, preferably two, or more than two, alcohol moieties (C—OH). The alcohol moieties may be located along a backbone of the oligomer. The alcohol moieties may be located at an end of the oligomer. In a detailed embodiment, the oligomer terminates with an alcohol moiety. In one or more embodiments, the modifying oligomer excludes compounds having silanol (Si—OH) groups.

Isocyanate index is defined as the molar ratio of the total isocyanate groups in the diisocyanate to the total hydroxyl and/or amino groups presented in polyols and extenders. In general, the polyurethane becomes harder with an increasing isocyanate index. There is, however, a point beyond which the hardness does not increase and the other physical properties begin to deteriorate.

Principles and embodiments of the present invention relate generally to polyurethane materials having improved surface properties, and methods of preparing and using them. Provided are medical articles, for example, catheter tubing, that are self-lubricating and/or anti-fouling, which eliminates a need to separately provide functional coatings such as a lubricant and/or an anti-fouling agent. The articles comprise a polyurethane-based resin that is a reaction product of the following ingredients: a diisocyanate; a diol chain extender; a polyglycol; and a modifier incorporated into a backbone of the polyurethane-based resin or as a side chain. The backbone is formed by the diisocyanate, the polyglycol, and the diol chain extender. The modifier so incorporated may be referred to as a modifying oligomer.

A modifying oligomer for the backbone may be a diol-containing perfluoropolyether (PFPE). A modifying oligomer for the as a side chain may be a monofunctional polysiloxane (e.g., monodialcohol-terminated polydimethylsiloxane).

Combinations of modifying oligomers are also included in this disclosure. In an embodiment, a polyurethane-based resin is a reaction product of: a diisocyanate; a diol chain extender; a polyglycol; and a diol-containing perfluoropolyether. In an embodiment, a polyurethane-based resin is a reaction product of: a diisocyanate; a diol chain extender; a polyglycol; and a monofunctional polysiloxane (e.g., monodialcohol-terminated polydimethylsiloxane). In an embodiment, a polyurethane-based resin is a reaction product of: a diisocyanate; a diol chain extender; a polyglycol; a diol-containing perfluoropolyether; and a monofunctional polysiloxane (e.g., monodialcohol-terminated polydimethylsiloxane).

Polyurethane-based resins disclosed herein have enhanced soft segments. The resins in this disclosure are synthesized by a conventional one-step copolymerization process. No catalyst or solvent is required. The synthesis can also be achieved by a variety of other synthesis techniques with or without catalyst/solvent understood by those skilled in the art. The copolymerization process is expected to produce a more uniform polymer system and PFPE-based and/or monodialcohol-terminated PDMS soft segments are likely to drive polymer chain block phase separation with PFPE and/or PDMS moieties migrating onto the polyurethane surface to render the resulting medical article desirable surface properties, which are not inherent using coating technology. Through structural and compositional design, the resulting resins possess inherent lubricious and/or anti-fouling surface properties for medical device applications, thus no post-coating process is required.

Polyurethanes

Polyurethane materials disclosed herein have enhanced surface properties, which may be tailored to fit different practical needs. Medical devices formed of these polyurethane materials are used to create a fluid channel from a medication reservoir to a patient in need thereof, where the fluid channel may be inserted into and in fluid communication with vascular vessels, or subcutaneous tissue, where the invasive medical device comprises any of the polyurethane materials as described herein.

An advantage of these polyurethane materials is that they are self-lubricating and/or anti-fouling.

Thermoplastic polyurethanes (TPUs) suitable for medical devices are typically synthesized from three basic components, a diisocyanate, a polyglycol, and a chain extender, usually a low molecular weight diol, diamine, amino alcohol or water. If the chain extender is a diol, the polyurethane consists entirely of urethane linkages. If the extender is water, amino alcohol or diamine, both urethane and urea linkages are present, which results in a polyurethaneurea (PUU). Inclusion of an amine-terminated polyether to the polyurethane synthesis also results in a polyurethaneurea. Device applications for thermoplastic polyurethanes include central venous catheters (CVCs), peripherally inserted central catheter (PICCs), and peripheral intravenous catheters (PIVCs).

Polyurethane and polyurea chemistries are based on the reactions of isocyanates with other hydrogen-containing compounds, where isocyanates are compounds having one or more isocyanate group (—N=C=O). Isocyanate compounds can be reacted with water ($H_2O$), alcohols (R—OH), carboxylic acids (R—COOH), amines ($R_x$—$NH_{(3-x)}$), ureas (R—NH—$CONH_2$), and amides (R—$CONH_2$). Certain polyurethanes may be thermoplastic elastomers (TPE), whereas other compositions may be highly cross-linked.

Thermoplastic polyurethanes comprise two-phases or microdomains conventionally termed hard segments and soft segments, and as a result are often referred to as segmented polyurethanes. The hard segments, which are generally of high crystallinity, form by localization of the portions of the polymer molecules which include the diisocyanate and chain extender(s). The soft segments, which are generally either non-crystalline or of low crystallinity, form from the polyglycol or the optional amine-terminated polyether. The hard segment content is determined by the weight percent of diisocyanate and chain extender in the polyurethane composition, and the soft segment content is the weight percent of polyglycol or polydiamine. The thermoplastic polyurethanes may be partly crystalline and/or partly elastomeric depending on the ratio of hard to soft segments. One of the factors which determine the properties of the polymer is the ratio of hard and soft segments. In general, the hard segment contributes to hardness, tensile strength, impact resistance, stiffness and modulus while the soft segment contributes to water absorption, elongation, elasticity and softness.

Polyurethane materials may be used as raw materials for catheter tubing via compounding, extrusion/coextrusion or molding.

A base thermoplastic polyurethane may be produced by the reaction of: a diisocyanate, a diol chain extender, at least one polyglycol, optionally, an amine-terminated polyether, and a modifying oligomer. The polyurethane may have a hard segment content between about 25% and about 75% by weight, where a hard segment is the portion(s) of the polymer molecules which include the diisocyanate and the extender components, which are generally highly crystalline due to dipole-dipole interactions and/or hydrogen bonding. In contrast, the soft segments formed from the polyglycol portions and modifying oligomers between the diisocyanate of the polymer chains and generally are either amorphous or only partially crystalline due to the characteristics of the polyglycol(s) and modifying oligomer(s). In an embodiment, the hard segment content may be in the range of about 50% to about 75% and the soft segment content may be in the range of about 25% to about 50%.

Polymerization of the base polyurethane may be a one-step copolymerization process without requiring a catalyst, solvent or other additives. The synthesis can also be achieved by a variety of other synthesis techniques with or without catalyst/solvent understood by those skilled in the art.

The diisocyanate may be selected from the group consisting of: an aliphatic diisocyanate, alicyclic diisocyanate and an aromatic diisocyanate. In various embodiments, the isocyanate may be selected from the group consisting of: 4,4'-diphenylmethane diisocyanate (MDI), toluene diisocyanate (TDI), isophorone diisocyanate (IPDI), and methylene-bis(4-cyclohexylisocyanate) (HMDI), and combinations thereof.

The diol chain extender may be selected from the group consisting of: ethylene glycol, 1,3-propylene glycol, 1,4-butanediol, neopentyl glycol, and alicyclic glycols having up to 10 carbon atoms.

The polyglycol may be selected from the group consisting of: polyalkylene glycol, polyester glycol, polycarbonate glycol, and combinations thereof. In an embodiment, the polyglycol comprises the polyalkylene glycol. In an embodiment, the polyalkylene glycol comprises one or both of: a polytetramethylene ether glycol and a polyethylene glycol.

The polytetramethylene ether glycol may be of any desired molecular weight. The polytetramethylene ether glycol (PTMEG) may be PTMEG250, PTMEG650, PTMEG1000, PTMEG1400, PTMEG1800, PTMEG2000, and PTMEG2900. PTMEG has the formula: HO($CH_2CH_2CH_2CH_2$—O—$)_n$H, which may have an average value of n in the range of 3 to 40. A blend of two or more PTMEG250, PTMEG650, PTMEG1000, PTMEG1400, PTMEG1800, PTMEG2000, and PTMEG2900 may be used such. A preferred an average molecular weight of the combination is less than 1000 Da. In one or more embodiments, the polyols is a blend of two or more PTMEG having the formula: HO($CH_2CH_2CH_2CH_2$—O—$)_n$H, where n has an average value in the range of 3 to 40 and an average molecular weight of the combination being less than 1000 Da.

A further polyalkylene glycol may be polyethylene glycol (PEG) and/or polypropylene glycol (PPG). The PEG and/or PPG may be any desired molecular weight. In an embodiment, the PEG is: PEG4000. PEG4000 is a polyethylene glycol having an average molecular weight of 4,000 Da.

The polyurethane-based resin may further comprise a polyetheramine. Suitable polyetheramines include but are not limited to amine-terminated polyethers having repeating units of ethylene oxide, propylene oxide, tetramethylene oxide or combinations thereof and having an average molecular weight in the range of about 230 to 4000. Preferred polyetheramines have propylene oxide repeating units. Jeffamine® D4000 is a specific polyetheramine, a polyoxypropylene diamine, having an average molecular weight of about 4000.

The modifying oligomers contain functional moieties (e.g., fluoroether and/or silicone) that migrate onto the polyurethane surface to render the resulting medical article desirable surface properties and have at least one, preferably two, alcohol moieties (C—OH). In one or more embodiments, the modifying oligomer excludes compounds having silanol (Si—OH) groups.

A modifying oligomer for the backbone may be a diol-containing perfluoropolyether.

In one or more embodiments, the diol-containing perfluoropolyether has the following structure.

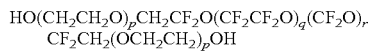

Wherein total of values for p+q+r are such that the fluorine content of the oligomer may be in the range of 55% to 60% by weight and the average molecular weight of the oligomer is in the range of 1500 to 2200 g/mol.

An exemplary diol-containing perfluoropolyether may be a commercial product sold under the trade name Fluorolink® E10-H, which is a dialcohol-terminated, ethoxylated PFPE, with about 1,700 Da average molecular weight and about 57% w/w fluorine content.

A modifying oligomer as a side chain may be a monofunctional polysiloxane. In one or more embodiments, the monofunctional polysiloxane is a monodialcohol-terminated polydimethylsiloxane (PDMS) having the following structure.

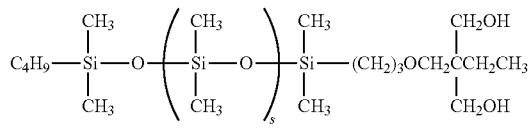

Values of s may be in the range of 5 to 200.

Exemplary monodialcohol-terminated polydimethylsiloxanes may be a commercial product sold under the product codes MCR-C61, MCR-C62 and MCR-C63. MCR-C62 has an average molecular weight of 5000 Da (s in range of 62-63), MCR-C61 has an average molecular weight of 1000 Da (s in range of 8-9), and MCR-C63 has an average molecular weight of 15,000 Da (s in range of 197-198). In one or more embodiments, the modifying oligomer for the as a side chain is MCR-C62.

The polyurethanes described herein may be fabricated into film, tubing, and other forms by conventional thermoplastic fabricating techniques including melt casting, compounding, extrusion/coextrusion, molding, etc. The polyurethane described herein may be used for PICCs, PIVCs, and CVCs. The polymer may have incorporated therein, as desired, conventional stabilizers, additives (e.g., a radiopaque filler), and/or processing aids. The amounts of these materials will vary depending upon the application of the polyurethane, but if present, are typically in amounts so ranging from 0.1 to 50 weight percent of the final compound.

General Procedure for Polyurethane Synthesis

The polyurethanes discussed here were prepared by a one-step copolymerization process using a pilot-scale polyurethane (PU) processor. The polyglycol(s), modifying oligomer(s), and chain extender(s) in the total amount of about 7.5 kg were charged into B tank (2.5 gallon full tank capacity with a recycle loop) of the PU processor with adequate mixing through both a tank agitator and the material recycle loop; the diisocyanate (calculated amount to react out B tank polyol mixture) was charged into A tank (2.5 gallon full tank capacity with a recycle loop) of the PU processor; during reaction, both B tank and A tank materials were pumped through their individual feeding lines at controlled feed rates to achieve an isocyanate index of 1.0 to 1.1; in one or more embodiments, the isocyanate index is 1.02; both the B and A streams were continuously injected through their respective injectors into a 8 cc mixing head with high rotor speed for adequate mixing and poured into silicone pans; the entire PU processor system, including A/B tanks, fill/feed/recycle/drain lines, injectors and mixing head, was maintained at a temperature of 50-90° C. (various zone temperature controls) and the tanks were pulled under vacuum of <100 mmHg during operation; the silicone pans filled with PU reactants mixture passed through a 150° F. conveyor oven with 10-20 min of curing time to achieve complete reaction; the resulting white PU slab has a dimension of 7.7 in×3.5 in×0.3 in. The PU slabs were subsequently grinded into granulated forms for downstream compounding and extrusion/coextrusion processes.

The PU granulates/chips can be extruded into ribbon sheets for mechanical and surface property characterizations. PU ribbon sheets can be extruded either from a single copolymer composition or from a blend of two or more different PU compositions. Blending/compounding approach will allow for quick creation and characterization of new PU compositions using the already existing PU copolymers. Even though the micro-domain structure and molecular weight distribution may be different using direct copolymerization approach compared to blending/compounding approach, we are expecting comparable mechanical and surface properties as they have the same overall PU composition. In one or more embodiments, blending/compounding approach was used for extrusion of certain PU ribbon compositions.

Table I. Exemplary Formulations of Polyurethane Resins with the proviso that the ingredients total 100%.

TABLE I

| Reactant | I-A by weight | I-B by weight | I-C by weight |
|---|---|---|---|
| Diisocyanate | 24-58% | 40-58% | 43-51% |
| Total Polyglycol | 15-75% | 15-50% | 25-45% |
| Diol Chain Extender | 0.1-18% | 9-18% | 11-15% |
| Modifying oligomer into backbone and/or side chain | 0.1-10% | 0.1-10% | 0.1-10% |
| Hard Segment % | 25-75% | 50-75% | 55-65% |

Exemplary Polyurethane-Based Resins

Medical articles are formed from a polyurethane-based resin, which is a reaction product of the following ingredients: a diisocyanate; a diol chain extender; a polyglycol; and a modifying oligomer comprising a diol-containing perfluoropolyether and/or a monofunctional polysiloxane, the diol-containing perfluoropolyether being incorporated into a backbone and the monofunctional polysiloxane being incorporated as a side chain of the polyurethane-based resin formed by the diisocyanate, the polyglycol, and the diol chain extender. In one or more embodiments, the polyglycol is one or more polyalkylene glycols, which may comprise one or both of: a polytetramethylene ether glycol and a polyethylene glycol. The resulting polyurethane-based resins are random copolymers based on the ingredients. A hard segment content is in the range of from 25% to 75% by weight, and a soft segment content of the resin is in the range of from 75% to 25% by weight.

Using the following ingredients, various polymer chain segments (A)-(E) are expected: the diisocyanate comprises 4,4'-diphenylmethane diisocyanate (MDI); the diol chain extender comprises 1,4-butanediol; the polyglycols comprise a polytetramethylene ether glycol (PTMEG) with MW range of 250-2900 Da (n=3-40), and optionally a polyethylene glycol with MW range of 200 to 8000 Da (m=4-182); the modifying oligomers comprise a diol-containing perfluoropolyether and/or a monofunctional polysiloxane. In one or more embodiments, the polyurethane-based resins are random copolymers comprising the following chain segments of (A) and (B); optionally (C); and one or both of: (D) and (E).

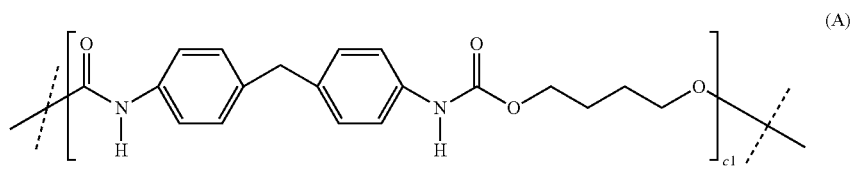

(A)

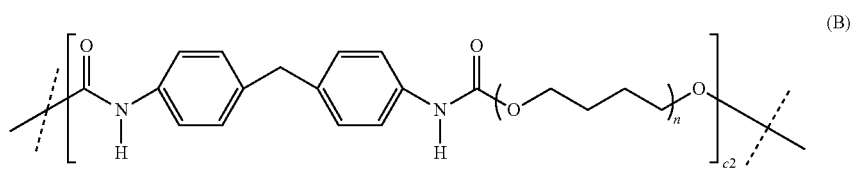

(B)

wherein n is in the range of 3 to 40;

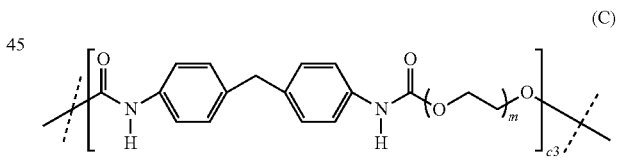

(C)

wherein m is in the range of 4 to 182;

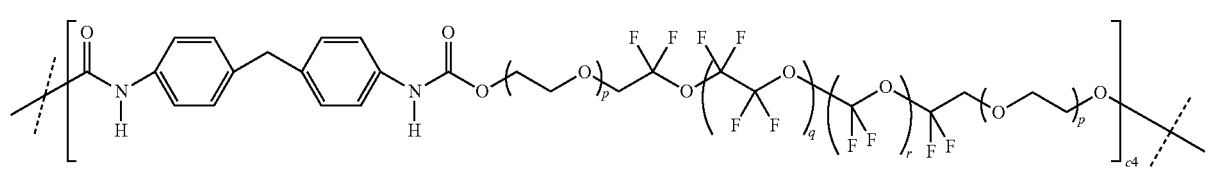

(D)

wherein the total of p+q+r is such that the fluorine content of the oligomer is in the range of 55% to 60% by weight and the average molecular weight of the oligomer is in the range of 1500 to 2200 g/mol;

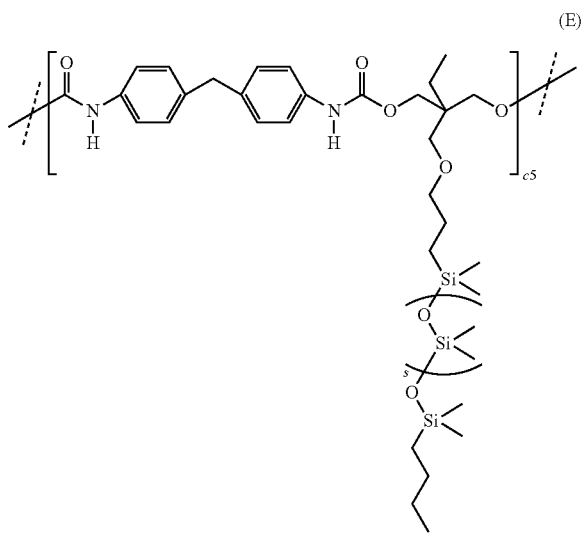

(E)

wherein s is in the range of 5 to 200.

In one or more embodiments, in the polyurethane-based resin the diisocyanate comprises 4,4'-diphenylmethane diisocyanate (MDI); the diol chain extender comprises 1,4-butanediol; the polyglycol comprises a polytetramethylene ether glycol (PTMEG); and the modifying oligomer comprises a diol-containing perfluoropolyether, thereby resulting in a random copolymer comprising chain segments of (A), (B), and (D).

In one or more embodiments, in the polyurethane-based resin the diisocyanate comprises 4,4'-diphenylmethane diisocyanate (MDI); the diol chain extender comprises 1,4-butanediol; the polyglycols comprise a polytetramethylene ether glycol (PTMEG) and a polyethylene glycol; and the modifying oligomer comprises a diol-containing perfluoropolyether, thereby resulting in a random copolymer comprising chain segments of (A), (B), (C), and (D).

In one or more embodiments, in the polyurethane-based resin the diisocyanate comprises 4,4'-diphenylmethane diisocyanate (MDI); the diol chain extender comprises 1,4-butanediol; the polyglycol comprises a polytetramethylene ether glycol (PTMEG); and the modifying oligomer comprises a monodialcohol-terminated polydimethylsiloxane (PDMS), thereby resulting in a random copolymer comprising chain segments of (A), (B), and (E).

In one or more embodiments, in the polyurethane-based resin the diisocyanate comprises 4,4'-diphenylmethane diisocyanate (MDI); the diol chain extender comprises 1,4-butanediol; the polyglycol comprises a polytetramethylene ether glycol (PTMEG); and the modifying oligomers comprise a diol-containing perfluoropolyether and a monodialcohol-terminated polydimethylsiloxane (PDMS), thereby resulting in a random copolymer comprising chain segments of (A), (B), (D), and (E).

In one or more embodiments, in the polyurethane-based resin the diisocyanate comprises 4,4'-diphenylmethane diisocyanate (MDI); the diol chain extender comprises 1,4-butanediol; the polyglycols comprise a polytetramethylene ether glycol (PTMEG) and a polyethylene glycol; and the modifying oligomer comprises a monodialcohol-terminated polydimethylsiloxane (PDMS), thereby resulting in a random copolymer comprising chain segments of (A), (B), (C), and (E).

In one or more embodiments, in the polyurethane-based resin the diisocyanate comprises 4,4'-diphenylmethane diisocyanate (MDI); the diol chain extender comprises 1,4-butanediol; the polyglycols comprise a polytetramethylene ether glycol (PTMEG) and a polyethylene glycol; and the modifying oligomers comprise a diol-containing perfluoropolyether and a monodialcohol-terminated polydimethylsiloxane (PDMS), thereby resulting in a random copolymer comprising chain segments of (A), (B), (C), (D), and (E).

Medical Articles

Medical articles may be any plastic part of a fluid path. Exemplary medical articles that may be formed by polyurethanes disclosed herein may be a component of a catheter; a needle/needleless connector; or tubing. Exemplary devices are: central venous catheters, peripherally-inserted central catheters, and peripheral intravenous catheters. Catheter tubing can be formed through compounding and extrusion/coextrusion processes. During compounding, granulates of synthesized base polyurethanes described herein, and an optional radiopaque filler are added into a twin-screw compounder simultaneously. The mix ratio can be controlled and adjusted by a gravimetric multiple-feeder system. The mixed polyurethane melt (conveying through multiple heating zones) continuously passes through a die, a quench tank, and is subsequently cut into regular-sized pellets by a puller-pelletizer. The collected pellets are used to be fed into an extruder/coextruder to form a catheter tube, depending on tubing's specific configuration.

EMBODIMENTS

Various embodiments are listed below. It will be understood that the embodiments listed below may be combined with all aspects and other embodiments in accordance with the scope of the invention.

Embodiment 1

A medical article formed from a polyurethane-based resin, which is a reaction product of the following ingredients: a diisocyanate; a diol chain extender; a polyglycol; and a modifying oligomer incorporated into a backbone, as a side chain, or both of the polyurethane-based resin formed by the diisocyanate, the polyglycol, and the diol chain extender, the modifying oligomer having an alcohol (C—OH) moiety and a functional moiety; wherein a hard segment content is in the range of from 25% to 75% by weight and a soft segment content of the resin is in the range of from 75% to 25% by weight; and wherein the medical article is effective as a self-lubricating and/or self-antifouling medical article.

Embodiment 2

The medical article of embodiment 1, wherein a concentration of the modifying oligomer of the polyurethane-based resin at a surface of the medical article is higher than a theoretical concentration based on uniform distribution of ingredients of the polyurethane-based resin.

Embodiment 3

The medical article of any preceding embodiment, wherein the functional moiety comprises a fluoroether, a silicone, or a combination thereof.

Embodiment 4

The medical article of any preceding embodiment, wherein the modifying oligomer is selected from the group consisting of: a diol-containing perfluoropolyether incorporated into the backbone, a monofunctional polysiloxane incorporated as the side chain, and combinations thereof.

Embodiment 5

The medical article of any preceding embodiment, wherein the modifying oligomer is present in an amount ranging from about 0.1 to about 10 weight percent of the overall composition of the polyurethane-based resin.

Embodiment 6

The medical article of any preceding embodiment, wherein the diisocyanate is selected from the group consisting of: an aliphatic diisocyanate, alicyclic diisocyanate and an aromatic diisocyanate.

Embodiment 7

The medical article of the preceding embodiment, wherein the diisocyanate is selected from the group consisting of: 4,4'-diphenylmethane diisocyanate (MDI), toluene diisocyanate (TDI), isophorone diisocyanate (IPDI), and methylene-bis(4-cyclohexylisocyanate) (HMDI), and combinations thereof.

Embodiment 8

The medical article of any preceding embodiment, wherein the diol chain extender is selected from the group consisting of: ethylene glycol, 1,3-propylene glycol, 1,4-butanediol, neopentyl glycol, and alicyclic glycols having up to 10 carbon atoms.

Embodiment 9

The medical article of any preceding embodiment, wherein the polyglycol is selected from the group consisting of: polyalkylene glycol, polyester glycol, polycarbonate glycol, and combinations thereof.

Embodiment 10

The medical article of the preceding embodiment, wherein the polyglycol comprises the polyalkylene glycol.

Embodiment 11

The medical article of the preceding embodiment, wherein the polyalkylene glycol comprises one or both of: a polytetramethylene ether glycol and a polyethylene glycol.

Embodiment 12

The medical article of the preceding embodiment, wherein the polyalkylene glycol comprises a polytetramethylene ether glycol, and a polyethylene glycol that comprises PEG4000.

Embodiment 13

A medical article formed from a polyurethane-based resin, which is a reaction product of the following ingredients: a diisocyanate; a diol chain extender; a polyglycol; and a modifying oligomer incorporated into a backbone, as a side chain, or both of the polyurethane-based resin formed by the diisocyanate, the polyglycol, and the diol chain extender; wherein a hard segment content is in the range of from 25% to 75% by weight and a soft segment content of the resin is in the range of from 75% to 25% by weight; and wherein the medical article has a contact angle with water that is 90° or greater.

Embodiment 14

The medical article of the preceding embodiment, wherein the modifying oligomer has an alcohol (C—OH) moiety and a functional moiety.

Embodiment 15

The medical article of the preceding embodiment, wherein the functional moiety comprises a fluoroether, a silicone, or a combination thereof.

Embodiment 16

The medical article of any of embodiment 13 to the preceding embodiment, wherein the modifying oligomer is selected from the group consisting of: a diol-containing perfluoropolyether incorporated into the backbone, a monofunctional polysiloxane incorporated as the side chain, and combinations thereof.

Embodiment 17

The medical article of any of embodiment 13 to the preceding embodiment comprising a concentration of the modifying oligomer of the polyurethane-based resin at a surface of the medical article is higher than a theoretical concentration based on uniform distribution of ingredients of the polyurethane-based resin.

Embodiment 18

The medical article of any of embodiment 13 to the preceding embodiment comprising a coefficient of static friction that is 0.28 or less.

Embodiment 19

The medical article of any of embodiment 13 to the preceding embodiment comprising a water sorption of 2.2% by weight or less.

Embodiment 20

The medical article of any of embodiment 13 to the preceding embodiment, which is non-hydratable.

Embodiment 21

The medical article of any of embodiment 13 to the preceding embodiment, which is effective to reduce bacterial biofilm colony formation.

Embodiment 22

The medical article of any of embodiment 13 to the preceding embodiment, wherein the polyglycol comprises a polyalkylene glycol comprising one or both of: a polytetramethylene ether glycol and a polyethylene glycol.

Embodiment 23

A method of infusion therapy comprising: infusing a material from a medical article according to any preceding embodiment into a patient.

Embodiment 24

The method of the preceding embodiment in the presence or absence of a separate lubricant coated on the medical article.

Embodiment 25

The method of embodiment 23 or 24 in the presence or absence of a separate anti-fouling agent coated on the medical article.

Embodiment 26

The method of the preceding embodiment in the absence of a separate anti-fouling agent coated on the medical article, wherein the medical article is effective for a reduced amount of thrombosis formation as compared to a medial article formed from a polyurethane-based resin, which is a reaction product of the following ingredients: a diisocyanate; a diol chain extender; a polyglycol in the absence of a modifying oligomer having an alcohol (C—OH) moiety and a functional moiety; wherein a hard segment content is in the range of from 25% to 75% by weight and a soft segment content of the resin is in the range of from 75% to 25% by weight.

EXAMPLES

Example 1

Various polyurethane resins were made in accordance with Table 1 by the one-step copolymerization process (no catalyst or solvent) using a pilot-scale polyurethane (PU) processor as described earlier in accordance with Exemplary Formulation I-C as shown above. Exemplary formulations have MDI as an aromatic diisocyanate, a combination of polytetramethylene ether glycols (PTMEGs with average equivalent molecular weight of 500-1000 Da) and optionally polyethylene glycol 4000 (PEG-4000) as the polyglycol mixture, 1,4-butanediol as the chain extender, and the modifying oligomer(s) according to Table 1. Reference polyurethanes without a modifying oligomer were made as well.

The modifying oligomers were selected from the group consisting of: dialcohol-terminated, ethoxylated perfluoropolyether (PFPE) (Fluorolink® E10-H) and monodialcohol-terminated polydimethylsiloxane (PDMS) (MCR-C62), and combinations thereof. Examples 1-A to 1-H are "mono-functional," incorporating only one modifying oligomer. Examples 1-I to 1-K are "bi-functional," incorporating two modifying oligomers. Examples 1-L to 1-N are references without modifying oligomers.

TABLE 1

| EXAMPLE | HARD SEGMENT CONTENT | MODIFYING OLIGOMER | LOCATION OF MODIFYING OLIGOMER | SOFT SEGMENT CONTENT |
|---|---|---|---|---|
| 1-A | 61.0 wt. % | Fluorolink® E10-H | Backbone | 1.77 wt. % of Fluorolink® E10-H<br>37.23 wt. % of PTMEG |
| 1-B-I | 61.0 wt. % | Fluorolink® E10-H | Backbone | 3.55 wt. % of Fluorolink® E10-H<br>35.45 wt. % of PTMEG |
| 1-B-II | 61.0 wt. % | Fluorolink® E10-H | Backbone | 3.55 wt. % of Fluorolink® E10-H<br>35.45 wt. % of PTMEG |
| 1-C | 61.0 wt. % | Fluorolink® E10-H | Backbone | 7.11 wt. % of Fluorolink® E10-H<br>31.89 wt. % of PTMEG |
| 1-D | 61.0 wt. % | Fluorolink® E10-H | Backbone | 1.77 wt. % of Fluorolink® E10-H<br>1.77 wt. % of PEG-4000<br>35.46 wt. % of PTMEG |
| 1-E | 61.0 wt. % | MCR-C62 | Side Chain | 1.77 wt. % of MCR-C62<br>37.23 wt. % of PTMEG |
| 1-F-I | 61.0 wt. % | MCR-C62 | Side Chain | 3.55 wt. % of MCR-C62<br>35.45 wt. % of PTMEG |
| 1-F-II | 61.0 wt. % | MCR-C62 | Side Chain | 3.55 wt. % of MCR-C62<br>35.45 wt. % of PTMEG |
| 1-G | 61.0 wt. % | MCR-C62 | Side Chain | 7.11 wt. % of MCR-C62<br>31.89 wt. % of PTMEG |
| 1-H | 61.0 wt. % | MCR-C62 | Side Chain | 1.77 wt. % of MCR-C62<br>1.77 wt. % of PEG-4000<br>35.46 wt. % of PTMEG |
| 1-I | 61.0 wt. % | Fluorolink® E10-H<br>MCR-C62 | Backbone<br>Side Chain | 1.18 wt. % of Fluorolink® E10-H<br>1.18 wt. % of MCR-C62<br>36.64 wt. % of PTMEG |
| 1-J | 61.0 wt. % | Fluorolink® E10-H<br>MCR-C62 | Backbone<br>Side Chain | 1.18 wt. % of Fluorolink® E10-H<br>1.18 wt. % of MCR-C62<br>1.18 wt. % of PEG-4000<br>35.46 wt. % of PTMEG |
| 1-K | 61.0 wt. % | Fluorolink® E10-H<br>MCR-C62 | Backbone<br>Side Chain | 1.77 wt. % of Fluorolink® E10-H<br>1.77 wt. % of MCR-C62<br>35.46 wt. % of PTMEG |
| 1-L REFERENCE | 61.0 wt. % | NONE | — | 39.0 wt. % of PTMEG |
| 1-M REFERENCE | 61.0 wt. % | NONE | — | 1.77 wt. % of PEG-4000<br>37.23 wt. % of PTMEG |
| 1-N REFERENCE | 61.0 wt. % | NONE | — | 3.55 wt. % of PEG-4000<br>35.45 wt. % of PTMEG |

Examples 1-B-I and 1-B-II have the same overall material composition. PU 1-B-I was prepared by direct copolymerization while PU 1-B-II was prepared by uniform blending/compounding of two different PUs (i.e., 50/50 wt. % blend of PUs 1-C and reference 1-L). Similarly, Examples 1-F-I and 1-F-II have the same overall material composition. PU 1-F-I was prepared by direct copolymerization while PU 1-F-II was prepared by blending/compounding (i.e., 50/50 wt. % blend of PUs 1-G and reference 1-L).

Table 2 shows gel temperatures and gel times for the copolymerization reactions according to Examples 1-B-I, 1-C, 1-F-I, 1-G, reference 1-L, and reference 1-N.

TABLE 2

| EXAMPLE | Gel temperature (° C.) | Gel time (second) |
|---|---|---|
| 1-B-I | 166 | 50.9 |
| 1-C | 176 | 47.4 |
| 1-F-I | 163 | 49.2 |
| 1-G | 181 | 48.9 |
| 1-L REFERENCE | 170 | 54.8 |
| 1-N REFERENCE | 166 | 49.9 |

Incorporation of a modifying oligomer during copolymerization did not reduce the overall reactivity of the reaction system. The copolymerization reactions of the inventive polyurethane resins proceeded as fast as the reference PU resins.

Example 2

Testing

For each example of Table 1, Polyurethane (PU) slabs (dimension of about 7.7 in×3.5 in×0.3 in) were produced from the above mentioned pilot-scale PU processor and conveyor oven curing system, which were subsequently grinded into granulated forms and extruded into ribbon sheets for material physical property characterizations. The thickness of the ribbon sheets was 0.004-0.008 in.

Tensile Property Testing. Tensile properties of both the reference and the inventive PU ribbons (thickness of 0.004-0.008 in.) were characterized using Instron. The testing was performed at room conditions (23° C., 50% RH, and >40 h equilibration time), which is provided in Table 3 (mean of 10 measurements for each data).

TABLE 3

| EXAMPLE | Tensile at break (psi) / Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) |
|---|---|---|---|---|---|---|---|
| 1-A | 9335.87 / 305.24 | 2488.68 | 2453.85 | 2771.02 | 3643.60 | 5950.87 | 575.11 |
| 1-B-I | 10431.46 / 348.21 | 3061.65 | 2835.57 | 3060.35 | 3852.15 | 6025.31 | 681.88 |
| 1-B-II | 11723.70 / 323.62 | 3136.57 | 2752.06 | 2970.45 | 3954.10 | 6769.87 | 738.48 |
| 1-C | 9107.09 / 293.95 | 3728.87 | 2737.82 | 2786.26 | 3560.44 | 5996.42 | 866.97 |
| 1-D | 9335.29 / 360.35 | 2475.80 | 2630.55 | 2874.52 | 3553.76 | 5417.62 | 538.06 |
| 1-E | 10001.34 / 292.44 | 2754.85 | 2557.02 | 2832.88 | 3808.26 | 6523.15 | 643.59 |
| 1-F-I | 9931.10 / 307.76 | 3062.44 | 2627.61 | 2817.42 | 3646.86 | 6202.49 | 681.71 |
| 1-F-II | 10710.55 / 308.63 | 3326.33 | 2660.70 | 2863.57 | 3800.39 | 6530.99 | 762.95 |
| 1-H | 10055.40 / 341.44 | 2648.25 | 2647.55 | 2925.06 | 3708.15 | 5852.68 | 596.74 |
| 1-I | 11648.80 / 333.57 | 2968.35 | 2722.92 | 3006.75 | 3983.96 | 6629.36 | 684.66 |
| 1-J | 9720.48 / 329.62 | 2675.00 | 2654.75 | 2920.36 | 3723.50 | 5877.22 | 590.67 |
| 1-K | 10260.23 / 308.77 | 3146.99 | 2795.14 | 3031.32 | 3893.26 | 6475.68 | 696.93 |
| 1-L REFERENCE | 11003.46 / 306.27 | 2317.78 | 2537.44 | 2904.74 | 3932.39 | 6707.76 | 528.77 |
| 1-M REFERENCE | 10771.98 / 338.51 | 2098.89 | 2456.02 | 2851.97 | 3775.58 | 6142.58 | 476.41 |

TABLE 3-continued

| EXAMPLE | Tensile at break (psi) — Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) |
|---|---|---|---|---|---|---|---|
| 1-N REFERENCE | 8359.43 — 355.94 | 2065.87 | 2397.94 | 2641.15 | 3273.58 | 4995.22 | 435.13 |

Testing was also performed at body indwell conditions (37° C., saline solution equilibration for 4 hours), which is provided in Table 4 (mean of 10 measurements for each data). Soften ratio is defined according to the following Equation (1).

$$\text{Soften Ratio} = \frac{\text{Young's Modulus at Room Conditions} - \text{Young's Modulus at Body Indwell Conditions}}{\text{Young's Modulus at Room Conditions}} \times 100\% \qquad \text{Equation (1)}$$

TABLE 4

| EXAMPLE | Tensile at break (psi) — Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) | Soften Ratio (%) |
|---|---|---|---|---|---|---|---|---|
| 1-A | 9534.19 — 388.18 | 514.41 | 1031.70 | 1243.58 | 1665.79 | 3444.07 | 92.53 | 83.91 |
| 1-B-I | 9326.23 — 435.48 | 650.83 | 1223.77 | 1399.75 | 1781.23 | 3314.68 | 109.40 | 83.96 |
| 1-B-II | 10475.36 — 368.03 | 566.44 | 1118.45 | 1392.06 | 2005.20 | 4130.25 | 104.77 | 85.81 |
| 1-C | 8676.21 — 365.53 | 723.79 | 1235.77 | 1467.23 | 1961.91 | 3757.50 | 140.23 | 83.83 |
| 1-D | 7356.43 — 436.90 | 521.14 | 1089.67 | 1230.13 | 1512.84 | 2715.69 | 92.05 | 82.89 |
| 1-E | 9793.78 — 348.66 | 466.94 | 993.37 | 1255.29 | 1793.56 | 3916.68 | 85.59 | 86.70 |
| 1-F-I | 8929.89 — 362.25 | 536.55 | 1049.22 | 1272.20 | 1770.41 | 3624.96 | 98.63 | 85.53 |
| 1-F-II | 9145.75 — 350.18 | 539.28 | 1058.57 | 1318.56 | 1920.58 | 3928.11 | 95.64 | 87.46 |
| 1-H | 8870.28 — 414.18 | 582.27 | 1104.33 | 1277.61 | 1657.98 | 3169.39 | 105.36 | 82.34 |
| 1-I | 10135.94 — 372.62 | 552.58 | 1093.60 | 1331.49 | 1835.61 | 3820.71 | 100.69 | 85.29 |
| 1-J | 8709.39 — 400.95 | 613.74 | 1137.38 | 1314.39 | 1716.58 | 3281.68 | 112.83 | 80.90 |
| 1-K | 10813.34 — 412.76 | 583.37 | 1201.74 | 1439.83 | 1928.56 | 3749.18 | 94.87 | 86.39 |
| 1-L REFERENCE | 9500.22 — 343.55 | 408.47 | 992.86 | 1268.98 | 1820.49 | 3970.41 | 62.66 | 88.15 |
| 1-M REFERENCE | 8544.77 — 395.76 | 481.76 | 1000.01 | 1182.88 | 1544.04 | 3041.71 | 82.04 | 82.78 |
| 1-N REFERENCE | 6286.08 — 431.58 | 511.56 | 1025.95 | 1142.83 | 1379.75 | 2399.17 | 85.19 | 80.42 |

Data in Tables 3 and 4 show that inventive PUs 1-B-I and 1-B-II (same overall material composition, where PU 1-B-I was a single target PU composition and PU 1-B-II was a blend of two different PUs, i.e., 50/50 wt. % blend of PUs 1-C and reference 1-L) exhibited comparable tensile properties. Similarly, inventive PUs 1-F-I and 1-F-II exhibited comparable tensile properties.

By comparison of tensile properties of reference PUs 1-L, 1-M and 1-N both at room conditions and body indwell conditions, with increase of PEG-4000 content in PTMEG soft segment, material tensile at break decreased while material elongation at break increased; material Young's modulus at room conditions decreased while material Young's modulus at body indwell conditions increased, resulting in reduced soften ratio as defined in Equation (1). Similar trend can be observed by comparison of inventive PUs 1-A vs. 1-D, 1-E vs. 1-H and 1-I vs. 1-J.

Comparison of tensile properties of reference PU 1-L with inventive PUs 1-A, 1-B and 1-C both at room conditions and body indwell conditions shows that with introduction of modifying oligomer Fluorolink® E10-H, material tensile at break and elongation at break did not change significantly. However, with increase of modifying oligomer Fluorolink® E10-H content, material Young's modulus both at room conditions and body indwell conditions increased. Similar trend can be observed by comparison of reference PU 1-M with inventive PU 1-D.

Comparison of tensile properties of reference PU 1-L with inventive PUs 1-E and 1-F both at room conditions and body indwell conditions shows that with introduction of modifying oligomer MCR-C62, material tensile at break and elongation at break did not change significantly. However, with increase of modifying oligomer MCR-C62 content, material Young's modulus both at room conditions and body indwell conditions increased. Similar trend can be observed by comparison of reference PU 1-M with inventive PU 1-H.

Comparison of tensile properties of reference PU 1-L with inventive PUs 1-I and 1-K both at room conditions and body indwell conditions shows that with introduction of modifying oligomers Fluorolink® E10-H and MCR-C62, material tensile at break and elongation at break did not change significantly, but material Young's modulus both at room conditions and body indwell conditions increased.

Overall, after introduction of modifying oligomers Fluorolink® E10-H and/or MCR-C62, the inventive novel PUs exhibited desirable tensile properties for medical device applications.

X-Ray Photoelectron Spectroscopy (XPS) Surface Analysis.

Surface elemental analysis of both the reference and the inventive PU ribbons were characterized using Fisons Surface Science SSX-100 Model 206 ESCA/XPS Spectrometer. The X-ray source is monochromatic Al K-alpha radiation with photon energy of 1486.6 eV; electrons have a take-off angle of 35°, detecting surface depth of 6-7 nm. The PU ribbons were surface-cleaned with 70% IPA/30% de-ionized water and then annealed at 95° C. for 2 hours prior to XPS surface analysis. Table 5 shows elemental wt. % calculated based on material bulk composition in comparison with elemental wt. % based on XPS ribbon surface analysis (mean of 6 measurements for each data). XPS technique does not analyze hydrogen, thus hydrogen was also omitted in bulk composition calculation.

TABLE 5

| EXAMPLE | Elemental wt. % calculated based on bulk composition (%) | | | | | Elemental wt. % based on XPS ribbon surface analysis (%) | | | | |
|---|---|---|---|---|---|---|---|---|---|---|
| | C | O | N | F | Si | C | O | N | F | Si |
| 1-A | 71.62 | 21.43 | 5.86 | 1.09 | N/A | 49.77 | 19.84 | 2.27 | 28.12 | N/A |
| 1-B-I | 70.70 | 21.28 | 5.84 | 2.18 | N/A | 38.17 | 18.86 | 1.59 | 41.38 | N/A |
| 1-B-II | 70.70 | 21.28 | 5.84 | 2.18 | N/A | 42.83 | 18.94 | 2.21 | 36.02 | N/A |
| 1-C | 68.85 | 21.00 | 5.79 | 4.36 | N/A | 36.74 | 17.79 | 1.58 | 43.89 | N/A |
| 1-D | 71.37 | 21.69 | 5.85 | 1.09 | N/A | 43.75 | 20.12 | 1.93 | 34.21 | N/A |
| 1-E | 71.89 | 21.55 | 5.86 | N/A | 0.70 | 59.39 | 21.94 | 1.48 | N/A | 17.19 |
| 1-F-I | 71.24 | 21.52 | 5.85 | N/A | 1.39 | 48.85 | 23.33 | 0.82 | N/A | 27.00 |
| 1-F-II | 71.24 | 21.52 | 5.85 | N/A | 1.39 | 51.34 | 21.95 | 0.84 | N/A | 25.87 |
| 1-H | 71.64 | 21.81 | 5.85 | N/A | 0.70 | 57.63 | 23.52 | 1.39 | N/A | 17.47 |
| 1-I | 71.49 | 21.46 | 5.86 | 0.73 | 0.46 | 45.20 | 21.00 | 1.70 | 23.02 | 9.08 |
| 1-J | 71.33 | 21.64 | 5.85 | 0.73 | 0.46 | 43.34 | 21.05 | 1.30 | 23.10 | 11.20 |
| 1-K | 70.97 | 21.40 | 5.84 | 1.09 | 0.70 | 42.94 | 21.00 | 1.29 | 22.18 | 12.60 |
| 1-L REFERENCE | 72.54 | 21.57 | 5.88 | N/A | N/A | 73.66 | 24.98 | 1.36 | N/A | N/A |
| 1-M REFERENCE | 72.29 | 21.84 | 5.87 | N/A | N/A | 75.20 | 22.48 | 2.32 | N/A | N/A |
| 1-N REFERENCE | 72.04 | 22.11 | 5.85 | N/A | N/A | 72.34 | 26.56 | 1.10 | N/A | N/A |

Data in Table 5 show that inventive PUs 1-B-I and 1-B-II (same overall material composition, where PU 1-B-I was a single target PU composition and PU 1-B-II was a blend of two different PUs) exhibited comparable surface elemental contents. Similarly, inventive PUs 1-F-I and 1-F-II exhibited comparable surface elemental contents.

Based on XPS surface analysis of reference PUs 1-L, 1-M and 1-N, there is a higher concentration of polyglycol-based soft segment (proved by higher oxygen content) on the surface than its theoretical value and a lower concentration of urethane hard segment (proved by lower nitrogen content) on the surface than its theoretical value, due to the phase separation of soft and hard segments within PUs.

Based on XPS surface analysis of inventive PUs 1-A, 1-B and 1-C, there is a significantly higher concentration of Fluorolink® E10-H soft segment (proved by significantly higher fluorine content) on the surface than its theoretical value. It is worthwhile to point out that with 100% of Fluorolink® E10-H based PU chemistry on the surface, the maximum potential fluorine content based on XPS analysis (excluding hydrogen) should be 50.94 wt. %. Table 5 shows that introduction of only 1.77 wt. % of Fluorolink® E10-H (Example 1-A) gave a surface fluorine content of 28.12 wt.

%; introduction of only 3.55 wt. % of Fluorolink® E10-H (Example 1-B) gave a surface fluorine content of 41.38 wt. %, which has been close to its maximum theoretical value; further increase of Fluorolink® E10-H content to 7.11 wt. % (Example 1-C) only slightly increased the surface fluorine content to 43.89 wt. %. Thus we can conclude that introduction of less than 10 wt. % of Fluorolink® E10-H has been adequate to maximize the resulting PU surface property; introduction of higher than 10 wt. % of Fluorolink® E10-H modifying oligomer would not provide benefits in terms of surface property modification. Without intending to be bound by theory, such high fluorine content on material surface would improve its surface properties (hydrophobic, lubricious and/or antifouling).

Based on XPS surface analysis of inventive PUs 1-E and 1-F, there is a significantly higher concentration of MCR-C62 soft segment (proved by significantly higher silicon content) on the surface than its theoretical value. It is worthwhile to point out that with 100% of MCR-C62 based PU chemistry on the surface, the maximum potential silicon content based on XPS analysis (excluding hydrogen) should be 37.58 wt. %. Table 5 shows that introduction of only 1.77 wt. % of MCR-C62 (Example 1-E) gave a surface silicon content of 17.19 wt. %; introduction of only 3.55 wt. % of MCR-C62 (Example 1-F) gave a surface silicon content of 27.00 wt. %, which has been close to its maximum theoretical value. Thus we can conclude that similar to Fluorolink® E10-H, introduction of less than 10 wt. % of MCR-C62 has been adequate to maximize the resulting PU surface property; introduction of higher than 10 wt. % of MCR-C62 modifying oligomer would not provide benefits in terms of surface property modification. Without intending to be bound by theory, such high silicon content on material surface would improve its surface properties (hydrophobic, lubricious and/or antifouling).

Based on XPS surface analysis of inventive PUs 1-I and 1-K, there are significantly higher concentrations of Fluorolink® E10-H and MCR-C62 soft segments (proved by significantly higher fluorine and silicon contents) on the surface than their theoretical values. Table 5 shows that introduction of only 1.18 wt. % of Fluorolink® E10-H and 1.18 wt. % of MCR-C62 (Example 1-I) gave a surface fluorine content of 23.02 wt. % and silicon content of 9.08 wt. %; further increase of both Fluorolink® E10-H and MCR-C62 contents to 1.77 wt. % (Example 1-K) did not further increase the surface fluorine content and only slightly increased the surface silicon content to 12.60 wt. %. Thus we can conclude that introduction of less than 10 wt. % in total of Fluorolink® E10-H and MCR-C62 has been adequate to maximize the resulting PU surface property; introduction of higher than 10 wt. % in total of Fluorolink® E10-H and MCR-C62 modifying oligomers would not provide benefits in terms of surface property modification. Without intending to be bound by theory, such high fluorine and silicon contents on material surface would improve its surface properties (hydrophobic, lubricious and/or antifouling).

Based on XPS surface analysis of inventive PUs 1-A and 1-D, introduction of PEG-4000 in replace of original PTMEG soft segment could promote Fluorolink® E10-H migration onto surface. Table 5 shows that original Example 1-A has a surface fluorine content of 28.12 wt. %; however, Example 1-D (with 1.77 wt. % of PEG-4000 introduction) has a higher surface fluorine content of 34.21 wt. %. This is presumably due to the increased segment phase separation as Fluorolink® E10-H is hydrophobic and PEG-4000 is more hydrophilic than PTMEG. Similar trend can be observed by comparison of inventive PUs 1-E vs. 1-H and 1-I vs. 1-J, as MCR-C62 is also hydrophobic.

In addition, inventive PU ribbon examples 1-A to 1-K are much less transparent (white cloudy) compared to the reference PU ribbon examples 1-L to 1-N. Without intending to be bound by theory, this is likely due to the increased copolymer phase separation within the inventive PFPE- and/or PDMS-containing PUs by introduction of Fluorolink® E10-H and/or MCR-C62, which could consequently affect light scattering. This increased copolymer phase separation has been discussed with respect to XPS analysis above. Even though white cloudy, the inventive PFPE- and/or PDMS-containing PU ribbon examples 1-A to 1-K still show adequate transparency to see through for blood flashback identification when used for catheter tubing applications.

Coefficient of Static Friction.

A Coefficient of Friction Tester Model 32-25 was used for this testing. Coefficient of static friction was determined by measuring the angle at which the metal block surface began to slide against the reference and inventive PU ribbon surfaces as the incline was increased at a constant rate. The coefficient of static friction is numerically equivalent to the tangent of that angle, which is provided in Table 6 (mean of 15 measurements for each data).

TABLE 6

| EXAMPLE | COEFFICIENT OF STATIC FRICTION |
| --- | --- |
| 1-A | 0.2847 |
| 1-B-I | 0.2677 |
| 1-C | 0.2277 |
| 1-D | 0.2721 |
| 1-E | 0.1977 |
| 1-F-I | 0.2186 |
| 1-F-II | 0.2314 |
| 1-H | 0.2332 |
| 1-J | 0.2471 |
| 1-K | 0.2152 |
| 1-L REFERENCE | 0.2828 |

Data in Table 6 show that inventive PUs 1-F-I and 1-F-II (same overall material composition, where PU 1-F-I was a single target PU composition and PU 1-F-II was a blend of two different PUs) exhibited comparable surface coefficient of static friction.

Table 6 shows that introduction of 1.77 wt. % and even 3.55 wt. % of modifying oligomer Fluorolink® E10-H did not significantly change the material surface coefficient of static friction; however, introduction of 7.11 wt. % of modifying oligomer Fluorolink® E10-H (Example 1-C) reduced the material surface coefficient of static friction from 0.2828 down to 0.2277. On the other hand, introduction of only 1.77 wt. % of modifying oligomer MCR-C62 has been adequate to reduce material surface coefficient of static friction down to the level of around 0.2. Thus, both of the modifying oligomers Fluorolink® E10-H and MCR-C62 can provide lubricious surface property, but MCR-C62 is a more efficient modifying oligomer in this case. Overall, less than 10 wt. % in total of Fluorolink® E10-H and MCR-C62 has been adequate to maximize the resulting PU surface property.

Water Contact Angle.

The reference and inventive PU ribbons were surface-cleaned with 70% IPA/30% de-ionized water and then annealed at 95° C. for 2 hours prior to water contact angle measurement. Table 7 shows the water contact angle data (mean of 10 measurements for each data).

TABLE 7

| EXAMPLE | CONTACT ANGLE (°) |
|---|---|
| 1-A | 90.7 |
| 1-B-I | 92.7 |
| 1-B-II | 95.1 |
| 1-C | 101.2 |
| 1-D | 90.3 |
| 1-E | 96.7 |
| 1-F-II | 92.6 |
| 1-I | 92.7 |
| 1-J | 90.8 |
| 1-K | 91.7 |
| 1-L REFERENCE | 77.0 |
| 1-N REFERENCE | 81.2 |

Data in Table 7 show that inventive PUs 1-B-I and 1-B-II (same overall material composition, where PU 1-B-I was a single target PU composition and PU 1-B-II was a blend of two different PUs) exhibited comparable surface contact angle.

Table 7 shows that introduction of modifying oligomer Fluorolink® E10-H resulted in increased contact angle as the modified PU surface became more hydrophobic; with increase of modifying oligomer Fluorolink® E10-H content, contact angle (surface hydrophobicity) increased. Similarly, introduction of modifying oligomer MCR-C62 or both Fluorolink® E10-H and MCR-C62 also resulted in more hydrophobic PU surface and increased contact angle.

Water Sorption.

The reference and inventive PU ribbons went through the following procedures for water sorption measurements: (i) cut ribbons (5 replicates for each group of ribbon material) into rectangular shape (around 1.4 in. length and 0.51 in. width); (ii) dried all sample ribbon cuts in an oven at 95° C. overnight; (iii) weighed each dry ribbon cut; (iv) submerged each dry ribbon cut into 37° C. de-ionized water for 4 h; (v) immediately after taking the ribbon cut out of water, used a tissue paper to wipe off the surface free water and re-weighed the saturated ribbon cut; (vi) recorded all the pre-hydration and post-hydration weight data and calculated water sorption based on the following Equation (2).

$$\text{Water Sorption} = \frac{\text{Post Hydration Sample Weight} - \text{Dry Sample Weight}}{\text{Dry Sample Weigth}} \times 100\% \quad \text{Equation (2)}$$

Table 8 shows the water sorption data (mean of 5 measurements for each data).

TABLE 8

| EXAMPLE | WATER SORPTION (%) |
|---|---|
| 1-A | 1.86 |
| 1-B-II | 1.74 |
| 1-C | 1.83 |
| 1-D | 2.04 |
| 1-E | 1.93 |
| 1-F-I | 1.78 |
| 1-F-II | 1.81 |
| 1-H | 2.10 |
| 1-J | 1.75 |
| 1-K | 1.93 |
| 1-L REFERENCE | 2.28 |
| 1-N REFERENCE | 2.73 |

Data in Table 8 show that inventive PUs 1-F-I and 1-F-II (same overall material composition, where PU 1-F-I was a single target PU composition and PU 1-F-II was a blend of two different PUs) exhibited comparable water sorption.

Comparison of water sorption of reference PUs 1-L and 1-N, shows that introduction of PEG-4000 in replace of PTMEG soft segment resulted in increased water sorption of PU material. This is consistent with PEG-4000 is more hydrophilic than PTMEG. Similar trend can be observed by comparison of inventive PUs 1-A vs. 1-D and 1-E vs. 1-H.

Table 8 also shows that introduction of modifying oligomer Fluorolink® E10-H and/or MCR-C62 resulted in reduced water sorption due to hydrophobic property of Fluorolink® E10-H as well as MCR-C62.

Hydratability.

The reference and inventive PU ribbons went through the following procedures for hydratability measurements: (i) cut ribbons (5 replicates for each group of ribbon material) into rectangular shape (around 1.4 in. length and 0.51 in. width); (ii) measured the dimensions (length and width) of each ribbon cut; (iii) submerged each ribbon cut into 37° C. saline solution for 4 h; (iv) immediately after taking the ribbon cut out of saline solution, re-measured the dimensions (length and width) of each saturated ribbon cut; (v) recorded all the pre-hydration and post-hydration dimension data and calculated dimension changes based on the following Equation (3).

$$\text{Dimension Change} = \frac{\text{Post Hydration Sample Dimension} - \text{Original Sample Dimension}}{\text{Original Sample Dimension}} \times 100\% \quad \text{Equation (3)}$$

Table 9 shows the dimension change data (mean of 5 measurements for each data).

TABLE 9

| EXAMPLE | Dimension Change - Length (%) | Dimension Change - Width (%) |
|---|---|---|
| 1-B-I | 0.58 | 0.57 |
| 1-D | 0.42 | 0.37 |
| 1-F-I | 0.38 | 0.36 |
| 1-H | 0.24 | 0.43 |
| 1-J | 0.35 | 0.22 |
| 1-K | 0.44 | 0.27 |
| 1-L REFERENCE | 0.43 | 0.17 |
| 1-N REFERENCE | 0.64 | 0.50 |

Table 9 shows that both the reference and inventive PU ribbons exhibited dimension changes of less than 1% after hydration. Thus, all these PU materials are dimensionally stable upon hydration and can be categorized as non-hydratable materials.

Thermogravimetric Analysis (TGA).

The reference and inventive PU granulates/chips were analyzed using TA Instruments TGA Q500. For testing, 3 mg of each sample was heated from 25° C. to 800° C. at 10° C./min in Nitrogen gas. Table 10 shows the degradation temperatures (based on 1% and 5% weight losses) of both the reference and inventive PU materials.

TABLE 10

| EXAMPLE | Degradation T at 1% of Weight Loss (° C.) | Degradation T at 5% of Weight Loss (° C.) |
|---|---|---|
| 1-B-I | 266.8 | 299.6 |
| 1-C | 266.7 | 296.0 |
| 1-F-I | 275.9 | 304.6 |
| 1-G | 278.0 | 303.1 |

TABLE 10-continued

| EXAMPLE | Degradation T at 1% of Weight Loss (° C.) | Degradation T at 5% of Weight Loss (° C.) |
|---|---|---|
| 1-L REFERENCE | 263.2 | 295.9 |
| 1-N REFERENCE | 265.4 | 299.0 |

Table 10 shows that introduction of modifying oligomer Fluorolink® E10-H did not change thermal property of the resulting PU significantly; introduction of modifying oligomer MCR-C62 resulted in around 10° C. increase of the degradation temperature.

FIG. 1 shows an example of the TGA scan for the inventive PU 1-B-I.

Differential Scanning Calorimetry (DSC).

The reference and inventive PU granulates/chips were analyzed using TA Instruments DSC Q2000. For testing, 5 mg of each sample was used for heat/cool/heat cycles; Cycle 1=heat from 25° C. to 250° C. at 10° C./min; Cycle 2=cool from 250° C. to −50° C. at 10° C./min; Cycle 3=heat from −50° C. to 250° C. at 10° C./min. Table 11 shows the glass transition temperature ($T_g$, onset from heating Cycle 3), crystallization temperature ($T_c$, peak from cooling Cycle 2), melting temperature onset from heating Cycle 1 ($T_{m1}$), and melting temperature onset from heating Cycle 3 ($T_{m2}$) of both the reference and inventive PU materials.

TABLE 11

| EXAMPLE | $T_g$ (onsite from heating Cycle 3) ° C. | $T_c$ (peak from cooling Cycle 2) ° C. | $T_{m1}$ (onsite from heating Cycle 1) ° C. | $T_{m2}$ (onsite from heating Cycle 3) ° C. |
|---|---|---|---|---|
| 1-B-I | −1.4 | 146.8 & 113.3 | 207.5 | 192.1 |
| 1-C | 1.5 | 135.8 & 108.1 | 212.2 | 193.5 |
| 1-F-I | 14.5 | 98.5 | 208.3 | 132.5 |
| 1-G | 13.2 | 111.2 | 193.5 | 152.9 |
| 1-L REFERENCE | 10.8 | 84.8 | 135.1 | 124.4 |
| 1-N REFERENCE | 3.4 | 105.0 | 160.0 | 152.3 |

Fluorolink® E10-H modified PUs 1-B-I and 1-C showed two separate peaks in cooling Cycle 2, thus two individual $T_c$ are identified in Table 11; MCR-C62 modified PUs 1-F-I and 1-G showed a larger difference of $T_m$ based on heating Cycle 1 vs. heating Cycle 3; for $T_m$ endotherm, more than one endothermic transition were overlapped in some cases, which might be attributed to the disruption/dissociation of domains with short/long range orders as well as melting of microcrystallites of the hard segments. It is hard to completely differentiate these endothermic transitions individually, thus they were all combined together for analysis and only one onsite $T_m$ was reported as the result. These information will be useful and can be referenced for ribbon and tubing extrusion of the new inventive PU materials.

Figure 2:
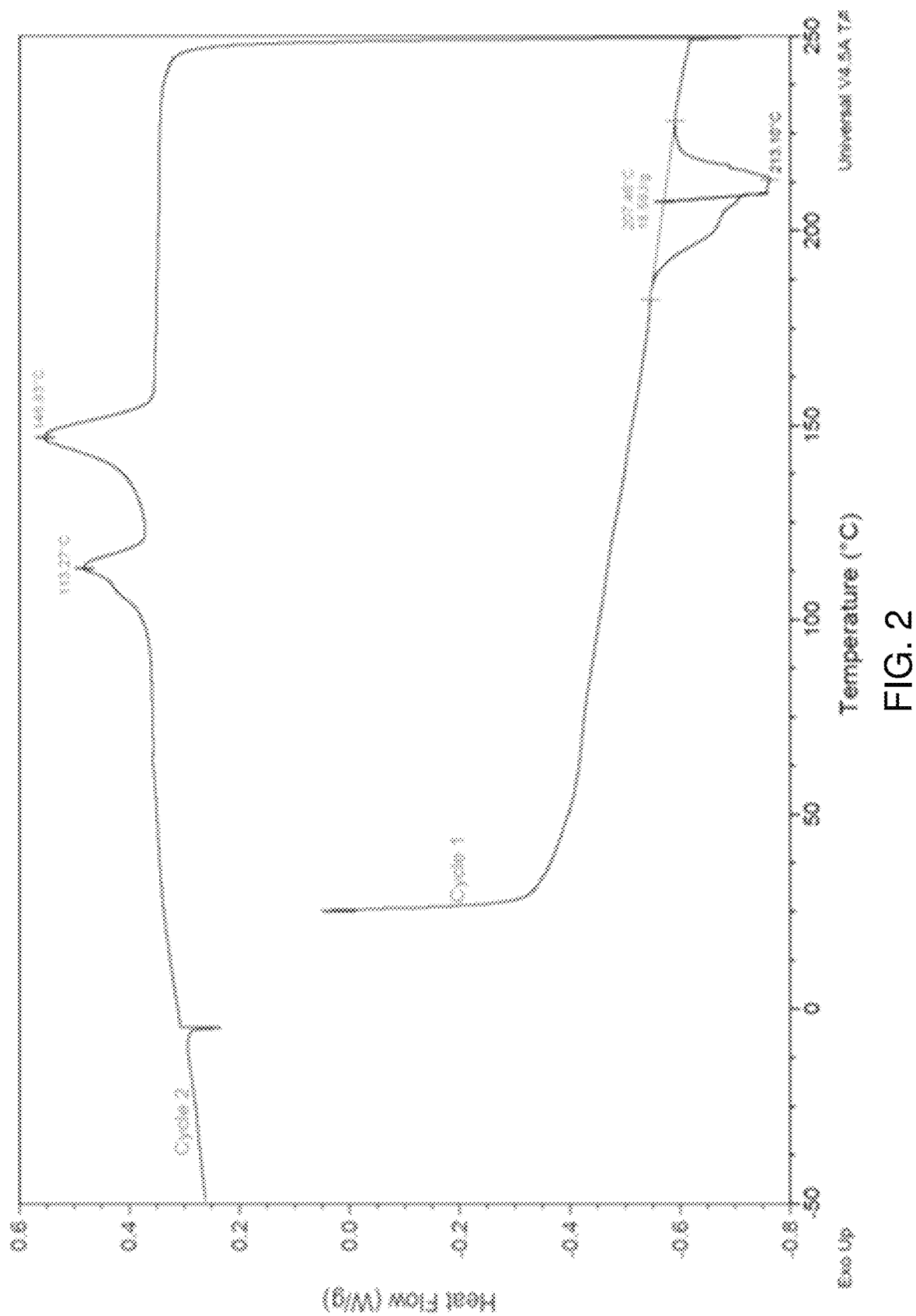
FIG. 2 is a Differential Scanning Calorimetry (DSC) scan of Cycle 1 and Cycle 2, heat flow (W/g) versus temperature (° C.) for an embodiment.
Figure 3:
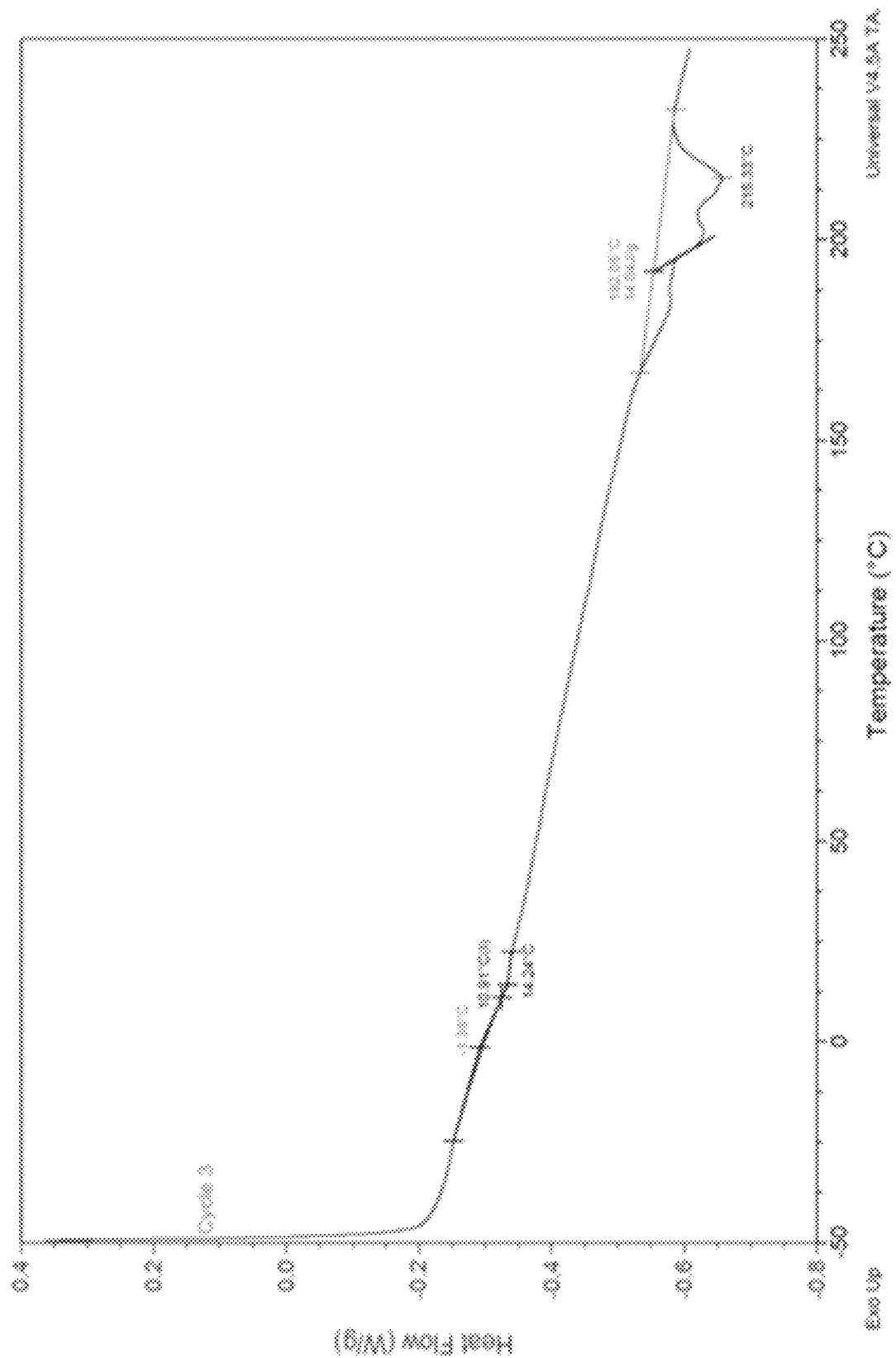
FIG. 3 is a Differential Scanning Calorimetry (DSC) scan of Cycle 3, heat flow (W/g) versus temperature (° C.) for an embodiment.

FIG. 2 is the DSC scan of Cycle 1 and Cycle 2 for the inventive PU 1-B-I. FIG. 3 is the DSC scan of Cycle 3 for the inventive PU 1-B-I.

Melt Flow Index.

The reference and inventive PU granulates/chips were characterized for melt flow indexes using a Zwick/Roell extrusion plastometer. The equipment has an extrusion barrel diameter of 9.55 mm (length of 170 mm) and a piston diameter of 9.48 mm (weight of 325 g). Five (5) g of each pre-dried (dried at 95-110° C. for over 12 hours) sample was used to perform the test at 220° C. with 5 kg of load weight and 300 seconds of preheat time. Table 12 shows the melt mass flow rate, melt volume flow rate and melt density of both the reference and inventive PU materials.

TABLE 12

| EXAMPLE | Melt Mass Flow Rate (g/10 min) | Melt Volume Flow Rate (cm³/10 min) | Melt Density (g/cm³) |
|---|---|---|---|
| 1-B-I | 36.11 | 34.20 | 1.056 |
| 1-C | 10.98 | 10.31 | 1.065 |
| 1-F-I | 10.71 | 10.33 | 1.037 |
| 1-G | 109.26 | 105.67 | 1.034 |
| 1-L REFERENCE | 11.60 | 11.17 | 1.039 |
| 1-N REFERENCE | 43.42 | 41.57 | 1.044 |

Table 12 shows that introduction of high density (1.69 g/cm³) modifying oligomer Fluorolink® E10-H resulted in higher melt density of the resulting PU material; melt flow rates of Fluorolink® E10-H modified PUs 1-B-I and 1-C are comparable with reference PUs 1-L and 1-N as only backbone type soft segments were used in these cases. Introduction of 3.55 wt. % of modifying oligomer MCR-C62 (Example 1-F-I) did not change the PU melt flow rate significantly; however, introduction of 7.11 wt. % modifying oligomer MCR-C62 (Example 1-G) resulted in significant increase of the resulting PU melt flow rate.

Biofilm Formation.

Figure 4:
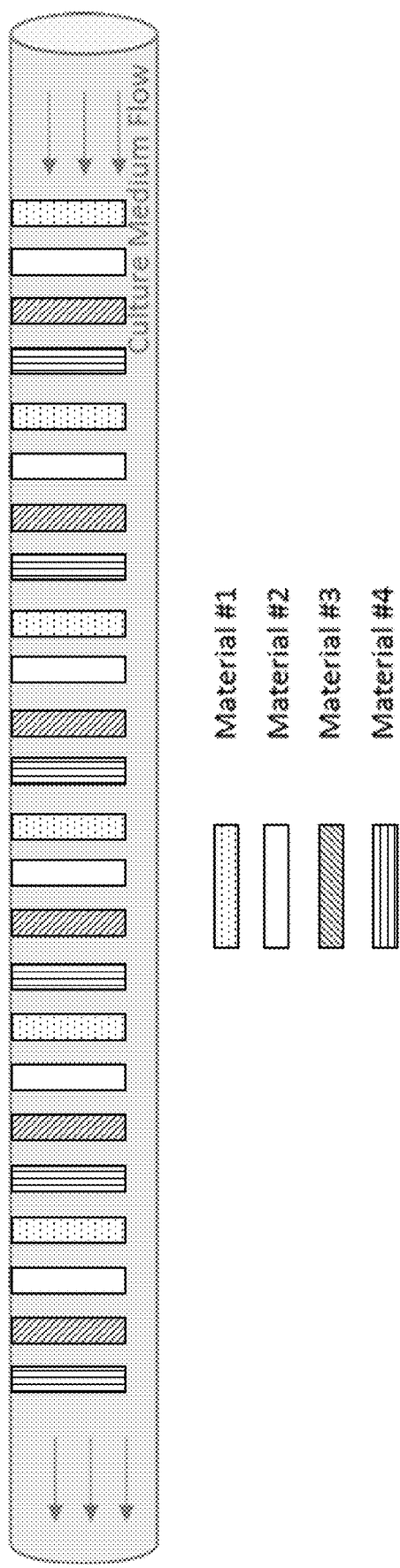
FIG. 4 is a schematic drawing of a chamber used for biofilm formation.

The reference and inventive PU ribbons were surface-cleaned with 70% IPA/30% de-ionized water and then annealed at 95° C. for 2 hours; afterwards, the ribbons were sealed in sterilization bags and went through a standard ethylene oxide sterilization process; the sterilized ribbon samples were used for biofilm formation testing. As shown in FIG. 4, a cylindrical transparent polycarbonate chamber with an inner diameter of 1.25 in. and a length of 21 in. was used in the testing; the reference and inventive PU ribbons were cut into small rectangular (7 mm by 25 mm) coupons and attached to caps which, when placed on the chamber suspended the coupons in the chamber; four different ribbon materials (6 replicates for each material) were tested at the same time for side by side comparison; the four different materials were placed inside the chamber at alternating positions (as shown in FIG. 4) for sample location randomization. Staphylococcus epidermidis was used as the bacterium for this testing. The testing procedures are as follows: filled bacteria/culture medium into the testing chamber which submerged all 24 testing coupons; incubated at 35° C. for 1 hour to allow bacteria to attach to coupons; gravity-fed 1500 ml of saline in 10 min to remove bacteria/culture medium from the chamber and then emptied the chamber; a peristaltic pump was used to circulate the culture medium between a culture medium reservoir and the chamber at 35° C. and a high shear of 1500 ml/min for 24 hours to allow biofilm formation; gravity-fed 2000 ml of saline in 13 min to remove culture medium from the chamber and then emptied the chamber; took out the coupons and each coupon was dipped in sterile saline once and then in another container of sterile saline for three additional times; bacterial biofilms on each coupon were then recovered into saline solution by vortexing and sonicating; enumerated bacterial colony counts by performing 10-fold serial dilutions; aliquots of each dilution were then cultured by the spread plate method; after incubation of the cultures, the plates were examined and the dilution that had colony counts between ~30 to 300 were counted; using the dilution factor, the initial total number of bacterial biofilms removed from the coupons could be calculated.

Tables 13 and 14 show the final bacterial biofilm colony counts on the reference and inventive PU ribbon coupons (mean of 6 replicate coupons for each material).

TABLE 13

| EXAMPLE | Bacterial Biofilm Colony Formation (CFU/Coupon) | Colony Formation Reduction (%) |
|---|---|---|
| 1-A | $3.83 \times 10^7$ | 25.63 |
| 1-B-II | $1.13 \times 10^7$ | 78.06 |
| 1-C | $2.28 \times 10^7$ | 55.73 |
| 1-L REFERENCE | $5.15 \times 10^7$ | — |

TABLE 14

| EXAMPLE | Bacteria Biofilm Colony Formation (CFU/Coupon) | Colony Formation Reduction (%) |
|---|---|---|
| 1-F-I | $1.39 \times 10^7$ | 50.00 |
| 1-L REFERENCE | $2.78 \times 10^7$ | — |

Data show that introduction of both modifying oligomers Fluorolink® E10-H and MCR-C62 resulted in certain reduction of bacterial biofilm colony formation, presumably due to the hydrophobic and lubricious surface making attachment difficult of various biological agents such as biofilms.

Example 3

For some compositions in Table 1 (inventive PUs 1-B-I, 1-C, 1-F-I, and reference PU 1-L), polyurethane granulates/chips were extruded into 22 GA standard single layer catheter tubing for further tubing property testing. After extrusion, the tubing was annealed at 90-95° C. for 1 hour. Similar as the previous ribbon findings, the inventive PU tubing samples 1-B-I, 1-C and 1-F-I are less transparent (cloudy) compared to the reference PU tubing sample 1-L. As described previously, this is presumably due to the increased copolymer phase separation within the inventive PFPE- and PDMS-modified PUs by introduction of Fluorolink® E10-H or MCR-C62, which could consequently affect light scattering. However, the inventive PFPE- and PDMS-modified PU tubing samples 1-B-I, 1-C and 1-F-I still showed adequate transparency to see through for blood flashback identification when used for catheter tubing applications.

Catheter Tubing Drag Force. The above mentioned inventive and reference 22 GA PU catheter tubing samples were assembled into catheter assemblies (using catheter tubing, wedge, catheter adapter, needle and needle hub). No catheter lube was applied outside of the catheter tubing during this testing. Catheter tubing drag force was tested using an Instron Universal Compression Tester. Natural rubber latex with a thickness of around 12 mils was used as the testing film. Table 15 shows the drag force of the inventive and reference PU catheter tubing materials against the natural rubber latex film (mean of 3-5 measurements for each data).

TABLE 15

| EXAMPLE | Catheter Tubing Drag Force (gram force) |
|---|---|
| 1-B-I | 13.67 |
| 1-C | 12.74 |
| 1-F-I | 10.11 |
| 1-L REFERENCE | 14.23 |

Table 15 shows similar trends as previous testing data as shown in Table 6 (coefficient of static friction). Introduction of the modifying oligomer Fluorolink® E10-H reduced the tubing drag force, but not very significant; however, introduction of modifying oligomer MCR-C62 can reduce the tubing drag force much more significantly. This is consistent with the previous conclusions of Table 6 that introduction of Fluorolink® E10-H and MCR-C62 can both provide lubricious surface property, but MCR-C62 is a more efficient modifying oligomer from lubricity point of view.

Surface Thrombogenicity Testing.

A standard chandler loop system was used to simulate the extracorporeal blood circulation. PVC tubes (¼ in. ID), partly filled with recalcified fresh bovine blood, were formed into re-closable loops and were rotated at a rotation speed of 20 rpm in a temperature controlled water bath (37° C.), to simulate arterial flow conditions. In the loops, various catheter tubing samples (22 GA and 4 inch length, through standard ethylene oxide sterilization process) were positioned to test interactions of blood with catheter tubing materials and surfaces. Thrombogenicity testing is a key component in the development of medical devices intended for contact with blood. In this study, we used the chandler loop model to evaluate its capacity to detect differential thrombogenic potential of different catheter tubing materials using recalcified fresh bovine blood.

Figure 5:
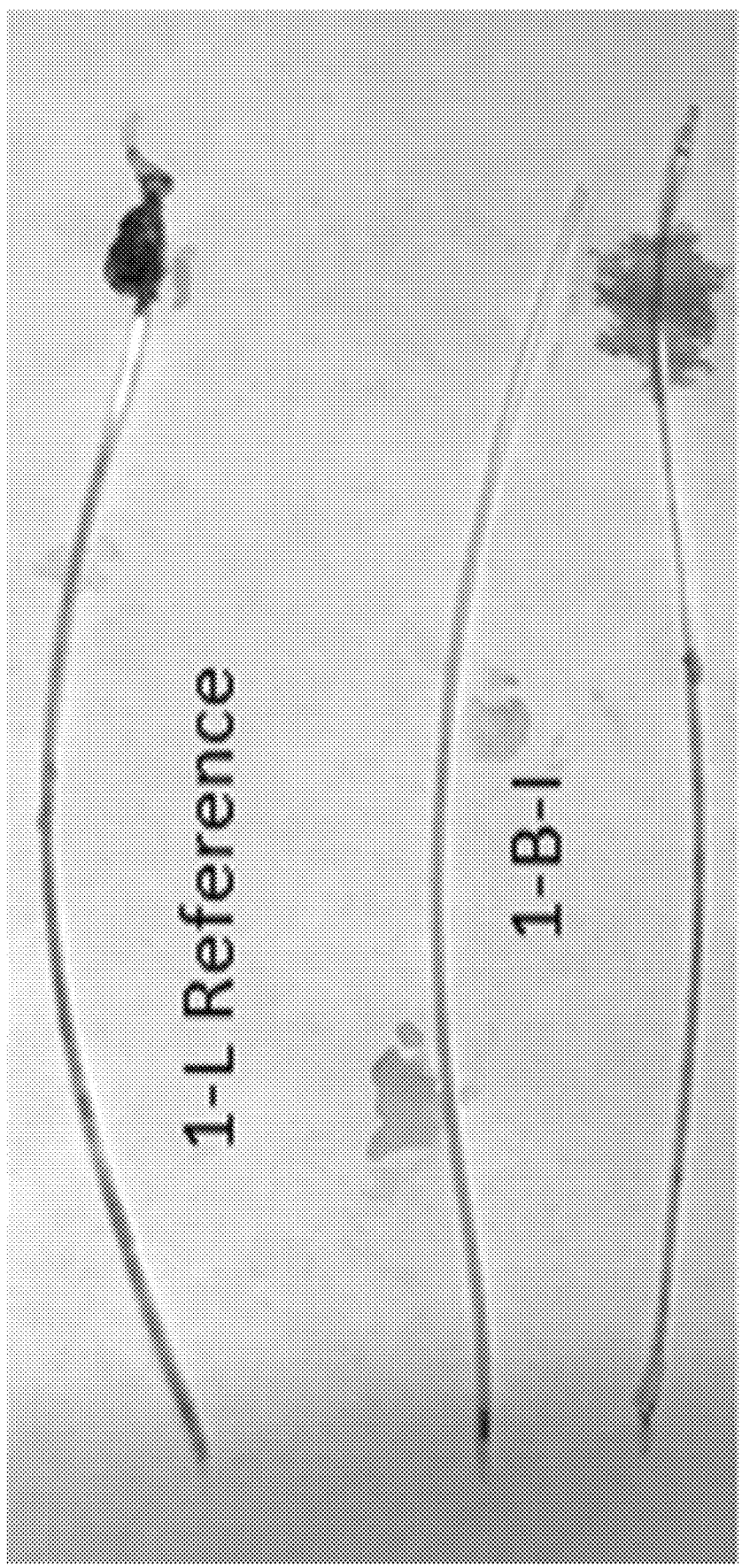
FIGS. 5-6 are annotated photographs showing thrombosis formation comparison among PU tubing materials according to embodiments herein versus a reference.

FIG. 5 is an annotated photograph showing thrombosis formation comparison of the inventive PU tubing materials 1-B-I and 1-F-I vs. the reference PU tubing material 1-L using chandler loop system with high heparin concentration of 1 unit/ml and testing time of 2 hr. FIG. 5 clearly shows that among these three materials, the inventive PU tubing material 1-B-I (introduction of 3.55 wt. % of modifying oligomer Fluorolink® E10-H) exhibited the best non-thrombogenic property; the inventive PU tubing material 1-F-I (introduction of 3.55 wt. % of modifying oligomer MCR-C62) exhibited relatively more thrombosis formation compared to the tubing material 1-B-I, but still better than the reference PU tubing material 1-L.

Figure 6:
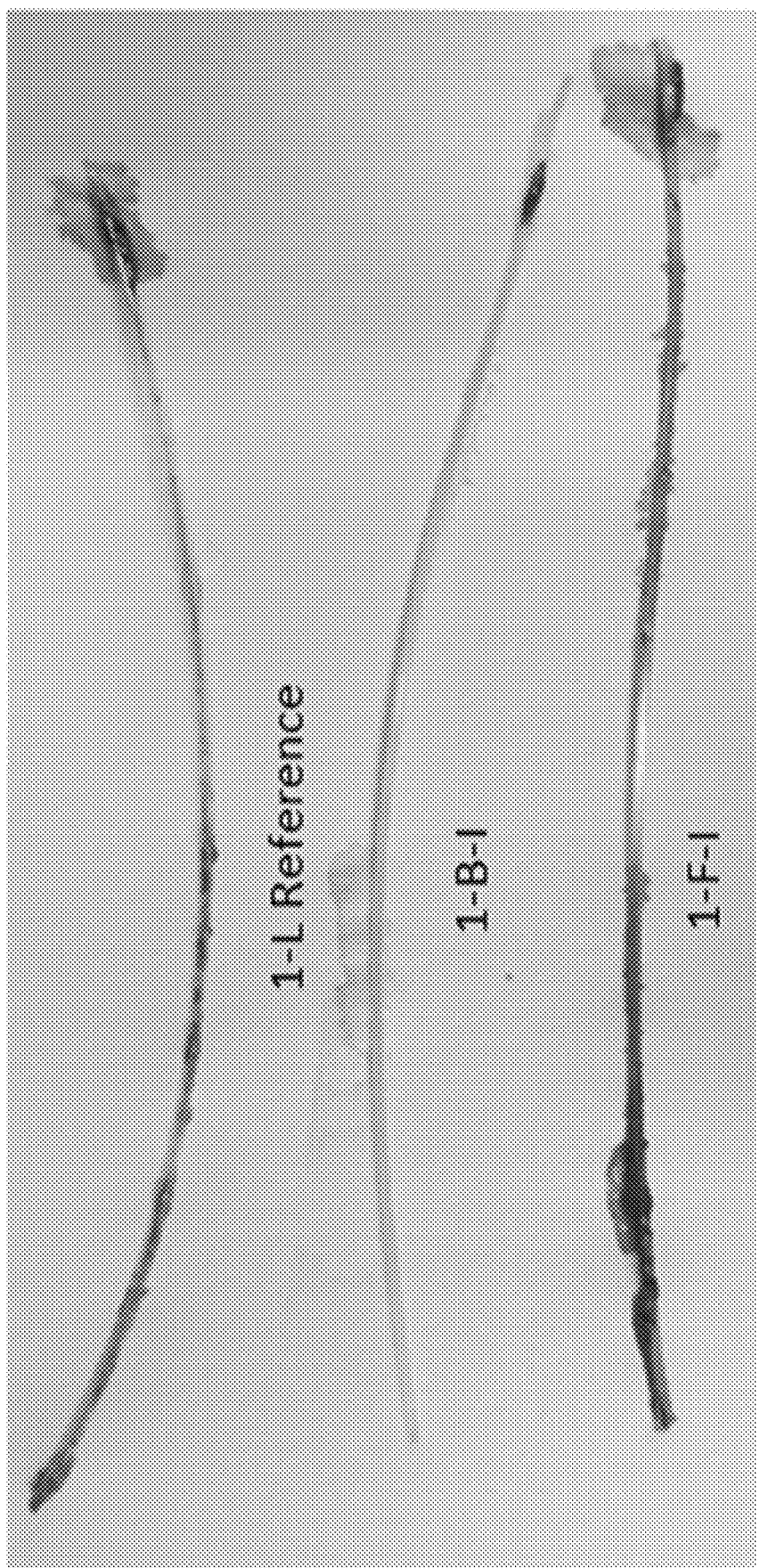

FIG. 6 shows thrombosis formation comparison of the inventive PU tubing materials 1-B-I and 1-F-I vs. the reference PU tubing material 1-L using chandler loop system with low heparin concentration of 0.2 unit/ml and testing time of 2 hr. FIG. 6 again shows that among these three materials, the inventive PU tubing material 1-B-I (introduction of 3.55 wt. % of modifying oligomer Fluorolink® E10-H) exhibited the best non-thrombogenic property; the inventive PU tubing material 1-F-I (introduction of 3.55 wt. % of modifying oligomer MCR-C62) could not be differentiated from the reference PU tubing material 1-L at such low heparin concentration.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical article formed from a polyurethane-based resin, which is a reaction product of the following ingredients:
   a diisocyanate;
   a diol chain extender;
   a polyglycol; and
   a modifying oligomer incorporated into a backbone, as a side chain, or both of the polyurethane-based resin formed by the diisocyanate, the polyglycol, and the diol chain extender, the modifying oligomer comprising a diol-containing perfluoropolyether incorporated into the backbone, the diol-containing perfluoropolyether having a structure of
   $HO(CH_2CH_2O)_pCH_2CF_2O(CF_2CF_2O)_q(CF_2O)_rCF_2CH_2(OCH_2CH_2)_pOH$
   wherein p+q+r provide a fluorine content in a range of 55% to 60% by weight and the average molecular weight of the modifying oligomer is in the range of 1500 to 2200 g/mol;
   wherein a hard segment content is in the range of from 25% to 75% by weight and a soft segment content of the resin is in the range of from 75% to 25% by weight; and
   wherein the medical article is effective as a self-lubricating and/or self-anti-fouling medical article.

2. The medical article of claim 1, wherein a concentration of the modifying oligomer of the polyurethane-based resin at a surface of the medical article is higher than a theoretical concentration based on uniform distribution of ingredients of the polyurethane-based resin.

3. The medical article of claim 1, wherein the modifying oligomer further comprises a monofunctional polysiloxane incorporated as the side chain, and combinations thereof.

4. The medical article of claim 1, wherein the modifying oligomer is present in an amount ranging from about 0.1 to about 10 weight percent of the overall composition of the polyurethane-based resin.

5. The medical article of claim 1, wherein the diisocyanate is selected from the group consisting of: an aliphatic diisocyanate, alicyclic diisocyanate, and an aromatic diisocyanate.

6. The medical article of claim 5, wherein the diisocyanate is selected from the group consisting of: 4,4'-diphenylmethane diisocyanate (MDI), toluene diisocyanate (TDI), isophorone diisocyanate (IPDI), and methylene-bis(4-cyclohexylisocyanate) (HMDI), and combinations thereof.

7. The medical article of claim 1, wherein the diol chain extender is selected from the group consisting of: ethylene glycol, 1,3-propylene glycol, 1,4-butanediol, neopentyl glycol, and alicyclic glycols having up to 10 carbon atoms.

8. The medical article of claim 1, wherein the polyglycol is selected from the group consisting of: polyalkylene glycol, polyester glycol, polycarbonate glycol, and combinations thereof.

9. The medical article of claim 1, wherein the polyglycol comprises the polyalkylene glycol.

10. The medical article of claim 1, wherein the polyalkylene glycol comprises one or both of: a polytetramethylene ether glycol and a polyethylene glycol.

11. The medical article of claim 1, wherein the polyalkylene glycol comprises a polytetramethylene ether glycol, and a polyethylene glycol that comprises PEG4000.

12. A method of infusion therapy comprising: infusing a material from a medical article according to claim 1 into a patient.

13. The method of claim 12, further comprising a separate lubricant coated on the medical article.

14. The method of claim 12, further comprising a separate antifouling agent coated on the medical article.

15. The method of claim 14, wherein the medical article is effective for a reduced amount of thrombosis formation as compared to a medial article formed from a polyurethane-based resin, which is a reaction product of the following ingredients: a diisocyanate; a diol chain extender; a polyglycol in the absence of a modifying oligomer having an alcohol (C—OH) moiety and a functional moiety; wherein a hard segment content is in the range of from 25% to 75% by weight and a soft segment content of the resin is in the range of from 75% to 25% by weight.

* * * * *